United States Patent [19]

Harbridge

[11] 4,258,050
[45] Mar. 24, 1981

[54] ANTIBACTERIAL AGENTS

[75] Inventor: John B. Harbridge, Coulsdon, England

[73] Assignee: Beecham Group Limited, England

[21] Appl. No.: 900,541

[22] Filed: Apr. 27, 1978

[30] Foreign Application Priority Data

Apr. 27, 1977 [GB] United Kingdom ............... 17660/77
Aug. 5, 1977 [GB] United Kingdom ............... 32835/77
Nov. 15, 1977 [GB] United Kingdom ............... 47394/77

[51] Int. Cl.³ .................. C07D 498/04; C07D 413/06
[52] U.S. Cl. ................................. 424/272; 260/245.3;
424/248.4; 424/269; 542/416; 542/434;
542/435; 542/443; 542/444; 542/445; 542/446;
542/436
[58] Field of Search ............... 542/416, 434, 435, 443,
542/444, 445, 446, 436; 424/272, 248.4, 269;
260/307 FA, 245.3

[56] References Cited
U.S. PATENT DOCUMENTS 4,078,067 3/1978 Christensen et al. ................. 424/272
4,079,177 3/1978 Harbridge et al. ................... 542/416

Primary Examiner—Arthur P. Demers
Attorney, Agent, or Firm—Jacobs & Jacobs

[57] ABSTRACT

Compounds of the formula (II):

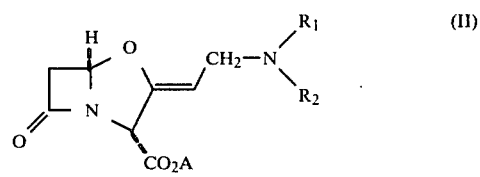

wherein A is a group such that $CO_2A$ is carboxylic acid, a non-toxic salt thereof or non-toxic ester thereof; $R_1$ is $COR_4$ or $OR_5$ wherein $R_4$ is lower alkyl, lower alkenyl, lower alkyl aryl or aryl and $R_5$ is $CO_2R_6$, $COR_6$ or $SO_2R_6$ wherein $R_6$ is lower alkyl, lower alkenyl, lower alkyl aryl or aryl; and $R_2$ is $COR_8$ wherein $R_8$ is lower alkyl, lower alkenyl, lower alkyl aryl or aryl; when $R_1$ is $COR_4$ and $R_2$ is $COR_8$, $R_4$ and $R_8$ are joined so that the $N(COR_4)$ $COR_8$ moiety is a 5-,6-, or 7-membered heterocyclic ring or said ring to which is fused a phenyl ring unsubstituted or substituted by one or two lower alkyl, lower alkoxyl, fluorine or chlorine; when $R_1$ is $OR_5$ and $R_2$ is $COR_8$, $R_5$ and $R_8$ are joined so that the $N(OR_5)$ $COR_8$ moiety is a 5-, 6-, or 7-membered heterocyclic ring, are useful for their antibacterial activity and as synergists for penicillins and cephalosporins.

149 Claims, No Drawings

ANTIBACTERIAL AGENTS

The present invention relates to novel antibacterial chemical compounds, to pharmaceutical compositions and to a process for the preparation of the new compounds.

Belgian Patent No. 827926 discloses inter alia that clavulanic acid, which has the formula (I):

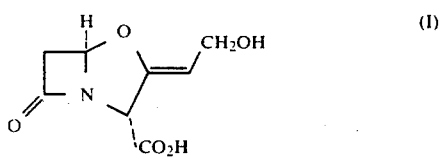

and its salts and esters have the ability to enhance the effectiveness of penicillins and cephalosporins against various β-lactamase producing bacteria by virtue of their ability to inhibit various β-lactamases.

A group of derivatives of clavulanic acid have now discovered which possess a different spectrum of β-lactamase inhibitory and antibacterial activity. These new compounds are able to inhibit the β-lactamase produced by various gram-negative and gram-positive bacteria such as Proteus sp., *Escherichia coli, Klebsiella aerogenes, Staphylococcus aureus* and the like.

The present invention provides the compounds of the formula (II):

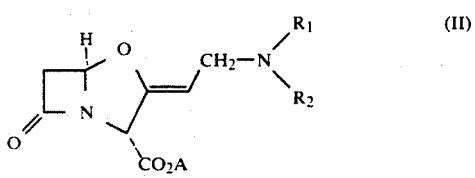

wherein A is a group such that $CO_2A$ is a carboxylic acid group or a salt or ester thereof; $R_1$ is a $CO_2R_3$ or $COR_4$ group or a $OR_5$ group where $R_3$ is a lower alkyl, lower alkenyl, lower alkyl aryl or aryl group, $R_4$ is a lower alkyl, lower alkenyl, lower alkyl aryl or aryl group and $R_5$ is a $CO_2R_6$, $COR_6$ or $SO_2R_6$ group where $R_6$ is a lower alkyl, lower alkenyl, lower alkyl aryl or aryl group; and $R_2$ is a hydrogen atom or a $CO_2R_7$ or $COR_8$ group where $R_7$ is a lower alkyl, lower alkenyl, lower alkyl aryl or aryl group and $R_8$ is a lower alkyl, lower alkenyl, lower alkyl aryl or aryl group; or when $R_1$ is a $COR_4$ group and $R_2$ is a $COR_8$ group, $R_4$ and $R_8$ may be joined so that the $N(COR_4)COR_8$ moiety is a 5-, 6-, or 7-membered heterocyclic ring to which may be fused a phenyl ring optionally substituted by one or two lower alkyl or lower alkoxyl groups or fluorine or chlorine atoms; or when $R_1$ is an $OR_5$ group and $R_2$ is a $COR_8$ group, $R_5$ and $R_8$ may be joined so that the $N(OR_5) COR_8$ moiety is a 5-, 6-, or 7-membered heterocyclic ring.

When used herein the term 'lower' means that the group contains up to 6 carbon atoms and preferably up to 4 carbon atoms, when used herein the term 'aryl' means phenyl or phenyl substituted by one or two groups selected from lower alkyl, lower alkoxyl, fluorine or chlorine. When attached directly to oxygen atoms the lower alkenyl group will not have the double bond on that carbon atom bearing the oxygen atom. When used herein the term 'alkyl' means unsubstituted alkyl and alkyl substituted by up to 3 halogen atoms or by hydroxyl (but not $C_1$ hydroxyl). More suitably "alkyl" means unsubstituted alkyl and alkyl substituted by up to 3 halogen atoms. However, when used herein the term alkyl preferably means unsubstituted alkyl.

When used herein "lower alkyl aryl" means a lower alkyl group substituted by an aryl group.

Suitably, $R_2$ is a $CO_2R_7$ or $COR_8$ group.

Suitably, $R_1$ is a $CO_2R_3$ or $CO.R_4$ group and $R_2$ is a $CO_2R_7$ or $COR_8$ group wherein $R_3$, $R_4$, $R_7$ and $R_8$ are as defined in relation to formula (II).

Suitably, $R_1$ is an $OR_5$ group wherein $R_5$ is as defined in relation to formula (II).

Suitable groups $R_1$ include $COCH_3$, $CO_2CH_3$, $CO.C_2H_5$, $CO_2C_2H_5$, $CO.CH=CH_2$, $CO.C_3H_7$, $CO_2C_3H_7$, $CO.C_3H_5$, $CO_2C_4H_9$, $CO.C_4H_9$, $CO.C_6H_5$, $CO_2C_6H_5$, $CO.C_6H_4.OCH_3$, $CO.CH_2C_6H_5$, $CO_2C_6H_4CH_3$, $CO_2CH_2C_6H_4CH_3$, $CO_2CH_2C_6H_4OCH_3$, $CO_2CH_2C_6H_4F$, $CO_2CH_2C_6H_3(OCH_3)_2$ or the like.

Suitable groups $R_2$ include those listed above as suitable groups $R_1$.

Other suitable groups $R_1$ include the $O.CO.CH_3$, $O.CO_2CH_3$, $O.SO_2CH_3$, $O.CO.C_2H_5$, $0.CO_2C_2H_5$, $O.SO_2C_2H_5$, $O.CO_2C_3H_7$, $O.CO_2C_4H_9$, $O.CO_2CH_2C_6H_5$, $O.SO_2.C_6H_4.CH_3$ and also $CO.CH_2Cl$.

Suitable diacyl derivatives within the formula (II) include those of the formula (III):

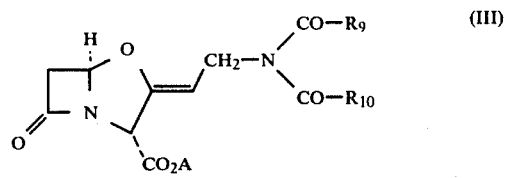

wherein A is as defined in relation to formula (II); $R_9$ is a lower alkyl, lower alkenyl, lower alkyl aryl or aryl group; and $R_{10}$ is a lower alkyl, lower alkenyl, lower alkyl aryl or aryl group or $R_9$ is joined to $R_{10}$ so that the $N(CO.R_9)COR_{10}$ moiety is a 5-, 6- or 7- membered heterocyclic ring to which may be fused a phenyl ring optionally substituted by one or two lower alkoxyl or lower alkyl groups or fluorine or chlorine atoms.

Suitable groups $R_9$ include the methyl, ethyl, n-propyl, iso-propyl, n-butyl, phenyl, benzyl, p-methoxyphenyl, alyl, vinyl and like groups.

Suitable groups $R_{10}$ include the methyl, ethyl, n-propyl, iso-propyl, n-butyl, phenyl, benzyl, p-methoxyphenyl, allyl, vinyl and like groups.

Suitable groups $R_9$ and $R_{10}$ when linked include $-CH_2.CH_2-$, $-CH=Ch-$, $-CH_2.CH_2.CH_2-$, phenylene, methoxyphenylene, methylphenylene and the like groups and $-NH-CO-$, $-N(CH_3)-CO-$ and the like groups.

A further suitable group of compounds within formula (III) include those of the formula (IV):

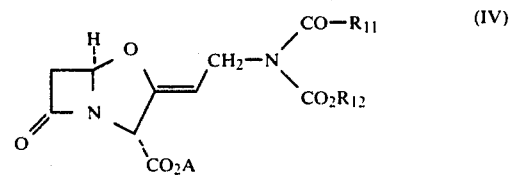

wherein A is as defined in relation to formula (II); $R_{11}$ is a lower alkyl, lower alkenyl, lower alkyl aryl or aryl group; and $R_{12}$ is a lower alkyl, lower alkenyl, lower alkyl aryl or aryl group or $R_{11}$ is joined to $R_{12}$ so that the $N(CO.R_{11})CO_2R_{12}$ moiety is a 5-, 6- or 7- membered heterocyclic ring to which may be fused a phenyl ring optionally substituted by one or two lower alkoxyl or lower alkyl groups or fluorine or chlorine atoms.

Suitable groups $R_{11}$ include the methyl, ethyl, n-propyl, iso-propyl, n-butyl, phenyl, benzyl, p-methoxybenzyl, allyl, vinyl and like groups Suitable groups $R_{12}$ include the methyl, ethyl, n-propyl, iso-propyl, n-butyl, phenyl, benzyl, p-methoxybenzyl, allyl and like groups.

Suitable groups $R_{11}$ and $R_{12}$ when linked include $-CH_2CH_2-$, $CH=CH$, phenylene, methoxyphenylene, methylphenylene and the like groups.

Favoured values for $R_{12}$ includes the benzyl and the substituted benzyl groups as such groups are useful intermediates in the preparation of the compounds of the formula (V). The benzyl group is particularly convenient for this purpose.

A further favoured group of compounds of this invention is that of the formula (V):

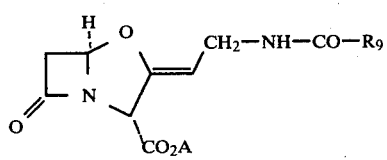

(V)

wherein A and $R_9$ are defined as in relation to formula (III).

Suitable values for $R_9$ in relation to formula (V) include those listed in relation to formula (III).

Yet another favoured group of compounds of this invention is that of the formula (VI):

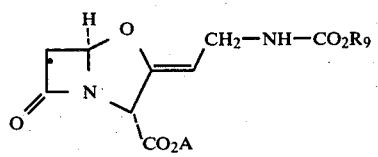

(VI)

wherein A and $R_9$ are defined in relation to formula (III) with the proviso that they are groups stable to hydrogenation.

Suitable groups $R_9$ in relation to formula (VI) include those described as suitable in relation to formula (III) except the benzyl, substituted benzyl and like hydrogenolysable groups.

A favoured group of compounds which may be prepared by a process of this invention is that of the formula (VII):

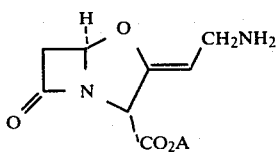

(VII)

wherein A is as defined in relation to formula (II).

The compounds of the formula (VII) are related to those of the formula (II), but differ chemically from them in that they have a basic $NH_2$ group while the compounds of the formula (II) have no basic nitrogen atom.

Of the compounds of the formula (VII) the preferred compound is that of the formula (VIII):

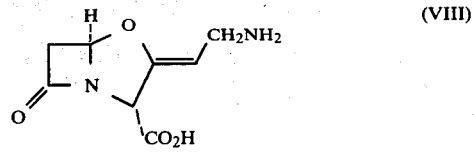

(VIII)

This compound exists as the zwitterion when solid and when in solution at non-extreme pH values such as between 4 and 7.

A particularly suitable form of the compound of the formula (VIII) is the crystalline form.

Suitably the compound of the formula (VIII) is at least 75% w/w pure.

Most suitably the compound of the formula (VIII) is provided in highly pure form, for example greater than 90% w/w and more suitably greater than 94% w/w, for example greater than 96% w/w.

The compound of the formula (VIII) has the advantage of providing extended blood levels after oral or parenteral administration. The crystalline compound of the formula (VIII) has the advantage of good storage stability especially when in highly pure form.

Salts and esters of the compound of the formula (VIII) are envisaged predominantly as intermediates in the preparation of the compound of the formula (VIII) per se. In general such compounds will be formed and further reacted in situ for example by neutralisation or de-esterfication.

Neutralisation of salts such as tosylates of the compound of the formula (VIII) may be by mildly basic insoluble resins such as IR 45 (OH) or Amberlyst A or the like.

Basic salts of the compound of the formula (VIII) are less favoured due to reduced stability.

Esters of the compound of the formula (VIII) are generally salted, for example by a pharmaceutically acceptable organic or inorganic acid such as hydrochloric, acetic or the like acid.

Another suitable group of compounds of this invention useful inter alia in the preparation of the compounds of the formula (V) is that of the formula (IX):

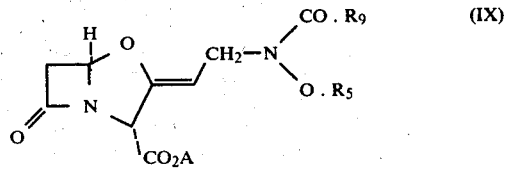

(IX)

wherein $R_9$ is as defined in relation to formula (III) and $R_5$ and A are as defined in relation to formula (II).

Suitable values for $R_9$ in relation to formula (IX) include those named in relation to formula (III).

Suitably $R_5$ is a $CO_2R_6$ or $COR_6$ group where $R_6$ is as defined in relation to formula (II). Suitably $R_5$ is a $SO_2R_6$ group where $R_6$ is as defined in relation to formula (II).

Suitable values for $R_5$ in relation to formula (IX) include those specifically named in relation to formula (II).

Another suitable group of intermediates in the preparation of compounds of the formula (VIII) is that of the formula (X):

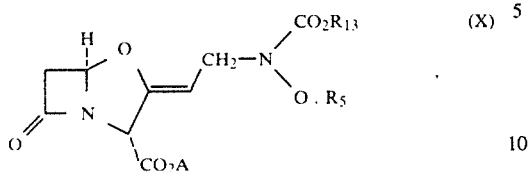

wherein A and $R_5$ are as defined in relation to formula (II) and $R_{13}$ is a benzyl group or substituted benzyl group.

Most suitably $R_{13}$ is a benzyl group.

Most suitably $R_5$ is a group referred to in relation to formula (IX).

The compounds of the formulae (II)–(VI) and (IX) and (X) wherein $CO_2A$ represents a carboxylic acid group or a salt thereof form a favoured aspect of this invention. An especially suitable part of this aspect is provided by the pharmaceutically suitable salts within formulae (II)–(VI) and (IX) and (X). Such salts include the sodium, potassium, calcium, magnesium, ammonium and other salts containing non-toxic cations. The sodium and potassium salts are particularly suitable. Such salts may be employed in the orally administrable compositions of this invention. Certain salts such as the sodium salts may also be employed in the injectable compositions of this invention. The lithium salts of the compounds of the formulae (II)–(VI) and (IX) and (X) are useful as intermediates in forming other salts such as the sodium, potassium and calcium salts by ion-exchange.

The compounds of the formulae (II)–(VI) and (IX) and (X) wherein $CO_2A$ represents a carboxylic acid ester group form an alternative favoured aspect of this invention. In addition to their use in the compositions of this invention the esters are also useful intermediates leading to the corresponding compound of the formulae (II)–(VI) and (IX) and (X) wherein $CO_2A$ is a carboxylic acid group or a salt thereof. Particularly suitable esters of the compounds of the formulae (II)–(VI) and (IX) and (X) include those wherein the group A is a group of the formula $A_1$ or $CHA_2A_3$ wherein $A_1$ is an alkyl group of 1–6 carbon atoms optionally substituted by an alkoxyl or acyloxyl group of 1–7 carbon atoms; $A_2$ is an alkenyl group of up to 5 carbon atoms or is a phenyl group optionally substituted by fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by fluorine, chlorine, bromine, nitro or alkyl or alkoxyl of up to 4 carbon atoms.

Certain favoured groups $A_1$ include the methyl, methoxymethyl, acetoxymethyl, acetoxyethyl, phthalidyl, ethoxycarbonyloxymethyl, α-ethoxycarbonyloxyethyl and the like groups.

Certain favoured groups $A_2$ include the phenyl and 4-methoxyphenyl groups. A further favoured group $A_2$ is the p-nitrobenzyl group. A particularly favoured moiety $A_3$ is the hydrogen atom.

The present invention also provides a process for the preparation of the compounds of the formula (II) as hereinbefore defined and also corresponding compounds wherein $R_1$ is a hydrogen atom which process comprises the reaction of (a) an ester of clavulanic acid; (b) a compound of the formula (XI):

wherein $R_1^1$ is a group $R_1$ as defined in relation to formula (II) and $R_2^1$ is a group $R_2$ as defined in relation to formula (II) excluding the hydrogen atom; (c) a compound of the formula (XII):

$$R_{14}O.CO.N=N.CO.OR_{15} \qquad (XII)$$

wherein $R_{14}$ and $R_{15}$ are independently lower alkyl, lower alkyl aryl or aryl; and (d) a compound of the formula (XIII):

wherein l, m and n are independently 0 or 1 and $R_{16}$, $R_{17}$ and $R_{18}$ are each independently a lower alkyl, lower alkyl aryl or aryl group; and thereafter if desired carrying out one or more of the following optional steps:

(a) converting a compound of the formula (II) wherein $R_1$ is an arylmethyloxycarbonyl group into a compound of the formula (II) wherien $R_1$ is a hydrogen atom by hydrogenation;

(b) converting a compound of the formula (II) wherein $R_2$ is an arylmethyloxycarbonyl group into a compound of the formula (II) wherein $R_2$ is a hydrogen atom by hydrogenation;

(c) converting an ester to a free or salted carboxylic acid group;

(d) converting a free or salted carboxylic acid group to an ester.

Suitable compounds of the formula (XIII) include those wherein the $R_{16}$, $R_{17}$ and $R_{18}$ groups are selected from methyl, ethyl, n-propyl, n-butyl, benzyl, phenyl and methoxyphenyl groups. It is generally convenient that $R_{16}$, $R_{17}$ and $R_{18}$ each represent the same moiety.

Favoured compounds of the formula (XIII) include triarylphosphines and trialkylphosphites.

Particularly suitable compounds of the formula (XIII) include triphenylphosphine, trimethylphosphite or triethyl phospite. A further particularly suitable compound of the formula (XIII) is tri-p-methoxyphenylphosphine.

Suitable compounds of the formula (XII) include those wherein $R_{14}$ and $R_{15}$ are independently selected from methyl, ethyl, propyl, butyl, phenyl, benzyl and like groups. It is generally convenient that $R_{14}$ and $R_{15}$ represent the same moiety.

Particularly suitable compounds of the formula (XII) include those wherein $R_{14}$ and $R_{15}$ each represent an ethyl or t-butyl group Suitable compounds of the formula (XI) may be selected from-:
$CH_3.CO.NH.CO.CH_3$
$CH_3.CO.NH.CO.C_2H_5$
$CH_3.CO.NH.CO.C_3H_7$
$C_2H_5.CO.NH.CO.C_2H_5$
$C_2H_5.CO.NH.CO.C_3H_7$ C$_3$H$_7$.CO.NH.CO.C$_3$H$_7$
CH$_3$.CO.NH.CO.C$_6$H$_5$
CH$_3$.CO.NH.CO.CH$_2$C$_6$H$_5$
C$_6$H$_5$.CO.NH.CO.C$_6$H$_5$
C$_6$H$_5$CH$_2$.CO.NH.CO.CH$_2$C$_6$H$_5$
CH$_3$.CO.NH.CO.CH=CH$_2$
CH$_3$.CO.NH.CO.C$_6$H$_4$OCH$_3$

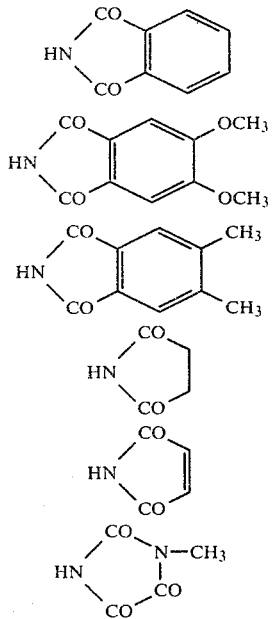

Other suitable compounds of the formula (XI) may be selected from:

CH$_3$.CO.NH.CO$_2$C$_2$H$_5$
CH$_3$.CO.NH.CO$_2$CH$_2$C$_6$H$_5$
CH$_3$.CO.NH.CO$_2$CH$_2$C$_6$H$_4$OCH$_3$
C$_2$H$_5$.CO.NH.CO$_2$C$_2$H$_5$
C$_2$H$_5$.CO.NH.CO$_2$CH$_2$C$_6$H$_5$
C$_3$H$_7$.CO.NH.CO$_2$CH$_2$C$_6$H$_5$
C$_2$H$_5$O$_2$C.NH.CO$_2$C$_2$H$_5$
C$_2$H$_5$O$_2$C.NH.CO$_2$CH$_2$C$_6$H$_5$
C$_6$H$_5$CH$_2$O$_2$C.NH.CO$_2$CH$_2$C$_6$H$_5$

Yet other suitable compounds of the formula (XI) may be selected from:

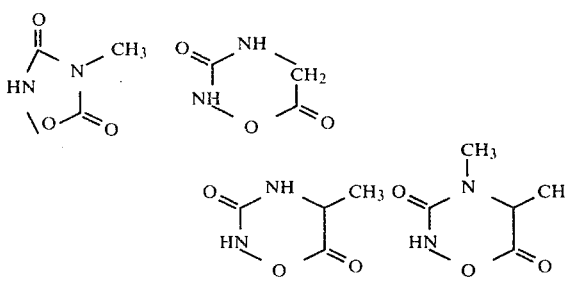

CH$_3$.CO.NH.O.CO.CH$_3$
CH$_3$.CO.NH.O.CO$_2$CH$_2$C$_6$H$_5$
CH$_3$.CO.NH.O.SO$_2$.CH$_3$
CH$_3$.CO.NH.O.SO$_2$CH$_2$C$_6$H$_5$
C$_6$H$_5$.CO.NH.O.SO$_2$CH$_3$
C$_6$H$_5$.CO.NH.O.SO$_2$C$_6$H$_5$

Any convenient ester of clavulanic acid may be used in the process of this invention but in general it is most suitable to use an ester of the formula (XIV) or (XV):

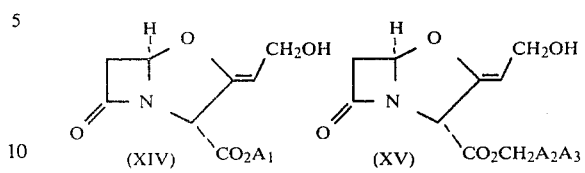

wherein A$_1$, A$_2$ and A$_3$ are as hereinbefore defined. Since it is frequently desirable to form a salt within formula (II), the ester of clavulanic acid employed is preferably one which is readily converted to the parent acid or its salt by mild methods of hydrolysis or hydrogenolysis. Thus particularly suitable esters of clavulanic acid for use in the process of this invention include methoxymethyl clavulanate, benzyl clavulanate and p-methoxybenzyl clavulanate (and also p-nitrobenzyl-clavulanate).

A preferred ester for use in this process is benzyl clavulanate.

In general roughly equal molar equivalents of the four reactants are employed in the process of this invention.

The reaction is performed in an inert organic solvent. The solvent used should be aprotic and unreactive towards the reagents involved. Suitable solvents include tetrahydrofuran (a preferred solvent), dioxane, ethyl acetate and the like. Other solvents include 1,2-dimethoxyethane and benzene.

Most suitably the process of this invention is carried out in an inert aromatic solvent such as an optionally substituted benzene.

Particularly suitable solvents for the process of this invention include benzene and toluene.

A preferred solvent for use in the process of this invention is benzene. The use of benzene as solvent has lead to improved yields of the condensation product.

Other aromatic solvents include chlorobenzene, fluorobenzene, methoxybenzene, bromobenzene, dimethylbenzene and the like.

The preceding inert aromatic solvents are particularly suitable for use with compounds of the formula (XI) wherein R$_1$$^1$ and R$_2$$^1$ are CO.OR$_1$$^2$ and CO.OR$_2$$^2$ groups where CO.OR$_1$$^2$ and CO.OR$_2$$^2$ are groups within R$^1$ and R$^2$. Most suitably R$_1$$^2$ and R$_2$$^2$ are aryl groups.

The reaction is normally carried out at a non-extreme temperature such as $-60°$ C. to $+100°$ C., more usually from about 5° C. to about 50° C., for example at approximately ambient temperature (such as about 12° C. to 25° C.).

It is frequently convenient to add a solution of the compound of the formula (XII) to a stirred solution of the other three reactants.

For those reaction using a compound of the formula (XIII) wherein l, m, and n are each 0, the reaction is generally complete within a short time of adding the compound of the formula (XII), for example normally within 2 hours, usually within 30 minutes and frequently virtually immediately. For those reactions using a compound of the formula (XIII) wherein l, m, and n are each 1 longer reaction times are required, for example up to 24 hours.

Once reaction is complete (e.g. as judged by the disappearance of the clavulanic ester on thin layer chromatography) the desired product ester may be obtained by evaporation of the solvent. The resulting solid or oil can be purified chromatographically if desired but it can also be triturated under an organic solvent such as diethyl ether to encourage crystallisation. When the oxidized form of the compound of the formula (XIII) employed is water soluble, for example oxidized trimethylphosphite or triethylphosphite, the reaction mixture can advantageously be washed with water as part of the purificiation system.

When formed in this manner the compounds of the formula (II) wherein $CO_2A$ is an ester group may be converted to a corresponding compound wherein $CO_2A$ is a carboxylic acid group or a salt thereof by hydrolysis or hydrogenolysis.

For those compounds of the formula (II) wherein $R_1$ and/or $R_2$ are hydrogenolysable groups (such as benzyloxycarbonyl or like groups) the method of forming the free or salted acid will normally be mild base hydrolysis if it is desired that the hydrogenolysable $R_1$ and/or $R_2$ group is maintained in the compound of the formula (II).

Suitable methods of hydrolysis of esters within formula (II) include mild base hydrolysis in aqueous solution. The reaction may be effected by maintaining the ester at a pH of 7.5 to 9.5 until hydrolysis is effected. Most suitably a readily hydrolysable ester such as the methoxymethyl ester is employed in this process. The pH may be maintained in the desired range in a pH-stat by the addition of a solution of a base such as LiOH, NaOH, KOH, $NaHCO_3$, $Na_2CO_3$ or the like at a rate that prevents accumulation of excess base which would cause the pH to increase unacceptably or by the use of a suspension of finely divided $Ca(OH)_2$, $Mg(OH)_2$, MgO, $MgCO_3$ or the like. Other bases which may be employed for hydrolysis include $Ba(OH)_2$, $Sr(OH)_2$ and the like.

Suitable methods of hydrogenolysis of ester within formula (II) include hydrogenation in the presence of a transition metal catalyst. Suitable hydrogenolysable esters include those of the formula (II) wherein $CO_2A$ is a group of the formula $CO_2CHA_2A_3$ as hereinbefore defined and of these the benzyl and p-methoxybenzyl esters are particularly suitable. The benzyl ester is a preferred ester. The pressure of hydrogen used in the reaction may be low, medium or high but in general an atmospheric or slightly super-atmospheric pressure of hydrogen is preferred. The transition metal catalyst employed is preferably palladium, for example palladium on charcoal, palladium on barium sulphate, palladium on calcium carbonate or the like. The hydrogenation may be effected in any convenient solvent in which the ester is soluble such as tetrahydrofuran or the like. Favoured organic solvents include tetrahydrofuran, lower alkanols (such as ethanol), mixtures of these solvents or said solvent or mixture together with a minor proportion of water. If this hydrogenation is carried out in the presence of a base then a salt within formula (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4OCOCH_3$, $Mg(OCOCH_3)_2$, $Mg(OCOH)_2$ and the like. If no base is present then hydrogenation leads to the preparation of an acid within formula (II) which may then be neutralised if desired to yield a salt. Suitable bases which may be used to neutralise acids within formula (II) include LiOH, NaOH, $NaHCO_3$, KOH, $Ca(OH)_2$, $Ba(OH)_2$, MgO, $Mg(OH)_2$, $NH_4OH$, $N(C_2H_5)_3$ and the like.

The lithium salts within formula (II) tend to be more easily prepared in pure crystalline form than other salts within formula (II). It is therefore often convenient to first form the lithium salt and then convert this into a further salt by ion-exchange, for example by passing a solution of the lithium salt through a bed of a cation exchange resin in sodium, potassium, calcium, ammonium or like form. Suitable cation exchange resins include Amberlite IR 120 and equivalent resins.

Crystalline salts within formula (II) can be hydrated.

The salts free acid within formula (II) may be converted to esters within formula (II) in conventional manner, for example by reaction with a reactive halide in solution in dimethylformamide or like solvvent. Esters may similarly be prepared by the reaction in an inert solvent of an acid within formula (II) with a diazocompound or with an alcohol in the presence of a condensation promoting agent such as dicyclohexylcarbodiimide.

This invention also provides a process for the preparation of a compound of the formula (V) as hereinbefore defined which process comprises the hydrogenation of a compound of the formula (XVI):

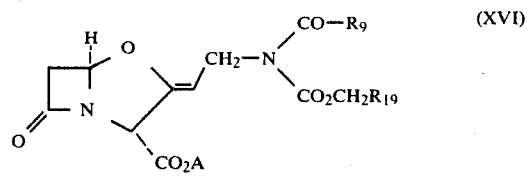

wherein A and $R_9$ are as defined in relation to formula (V) and $R_{19}$ is an aryl group and thereafter if desired converting an ester group into a free or salted caroxylic acid group or if desired converting an acid or salt into an ester.

Conveniently $R_{19}$ is a phenyl group.

The hydrogenation may be carried out as previously described for cleaving benzyl or like hydrogenolysable esters.

If the compound of the formula (XVI) is an ester which is cleaved by hydrogenation then cleavage of the ester group can occur at the same time as the replacement of the $CO_2CH_2R_{19}$ group. If a hydrogenolysable ester within the formula (V) is required this may be prepared from the corresponding acid or salt in conventional manner.

This invention further provides a process for the preparation of a compound of the formula (VI) as hereinbefore defined which comprises the hydrogenation of a compound of the formula (XVII):

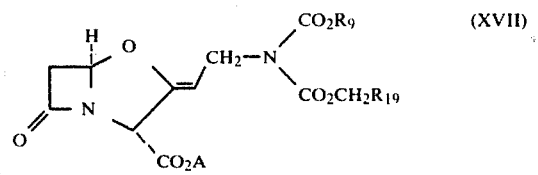

wherein A and $R_9$ are as defined in relation to formula (VI) and $R_{19}$ is an aryl group and thereafter if desired converting an ester group into a free or salted carboxylic acid group or if desired converting a free or salted carboxylic acid group into an ester.

Conveniently $R_{19}$ is a phenyl group.

The hydrogenation may be carried out as previously described for cleaving benzyl or like hydrogenolysable esters.

If the compound of the formula (XVII) is one in which $CO_2R_9$ is a hydrogenolysable group such as a $CO_2CH_2R_{19}$ group careful monitoring of the hydrogen uptake is required to ensure that the compound of the formula (VI) is not converted directly to a compound of the formula (VII). This is generally an inconvenient reaction as mixed products result.

Hydrogenolysable esters of the compounds of the formula (VI) may be prepared from the corresponding acid or a salt as hereinbefore defined.

In another aspect this invention provides a process for the preparation of a compound of the formula (VII) as hereinbefore defined which comprises the hydrogenation of an ester of a compound of a compound of the formula (XVIII):

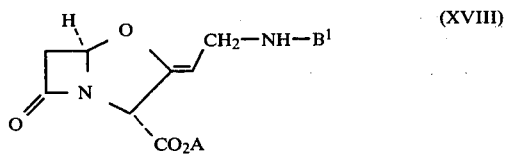

(XVIII)

wherein $B_1$ is a group which on hydrogenation is replaced by a hydrogen atom and A is as defined in relation to formula (VII) and thereafter, if desired, converting an ester group into a free or salted carboxylic acid group or if desired converting a free or salted carboxylic acid group into an ester.

Preferably, $B^1$ is a group $CO_2CH_2R_{19}$ where $R_{19}$ is an aryl group. Conveniently, $R_{19}$ is a phenyl group.

the hydrogenation may be carried out as previously described for cleaving benzyl or like hydrogenolysable esters.

In general the compound of the formula (XVIII) is produced in situ by hydrogenation of a compound of the formula (XVII) wherein $CO_2R_9$ and $CO_2CH_2R_{19}$ are both hydrogenolysable groups so that the compound of the formula (XVIII) has only transitory existence.

In general it is not necessary to isolate a compound of the formula (XVIII) but this may be done if desired. A suitable manner of preparation of a compound of the formula (XVIII) comprises hydrogenation of a compound of the formula (XVII) wherein $CO_2R_9$ is a hydrogenolysable group such as $CO_2CH_2C_6H_5$ or the like in the presence of a relatively weak catalyst such as palladium on barium sulphate. Careful monitoring of the reaction shows that the initial uptake of hydrogen is rapid and then soon slows down. The initial rapid uptake is believed due to the hydrogenation of the first hydrogenolysable group on the nitrogen atom. Stopping the reaction at this point yields the desired compound of the formula (XVIII). If the compound of the formula (XVIII) is a hydrogenolysable ester then continued hydrogenation leads to the preparation of a corresponding acid of the formula (XVIII) which may be neutralised to yield a salt in conventional manner.

The compounds of the formula (V) as hereinbefore defined may also be prepared by the hydrogenation of a correspondng compound of the formula (IX) as hereinbefore defined.

This hydrogenation reaction may also be performed as described for the hydrogenation of compounds of the formula (XVI).

The compounds of the formula (VI) as hereinbefore defined may also be prepared by hydrogenation of a corresponding compound of the formula (XIX):

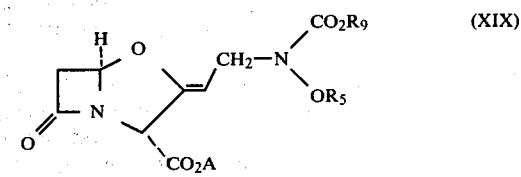

(XIX)

wherein A, $R_5$ and $R_9$ are as defined in relation to formula (IX).

This hydrogenation reaction may also be performed as described for the hydrogenation of the compounds of the formula (XVI).

Intermediates of the formula (XI) may be prepared in known manner, for example by (a) acylation of an amino compound; or (b) by reacting a compound of the formula (XX):

$R_1^1$—CO—NCO         (XX)

with an alcohol of the formula (XXI):

$R_2^1$—OH         (XXI)

wherein $R_1^1$ is a group within $R_1$ as defined in relation to formula (XI) other than the hydrogen atom and $R_2^1$ is as defined in relation to formula (XI). [See Tetrahedron Letter, Vol. 13, 1279-1282 (1972)] or by other conventional methods such as (c) the sulphonylation of a compound of the formula (XXII):

$R_1^1$—CO—NH—OH         (XXII)

wherein $R_1^1$ is as defined in relation to formula (XI).

A particularly preferred process of this invention comprises the hydrogenation in an organic solvent of a compound of the formula (XXIII):

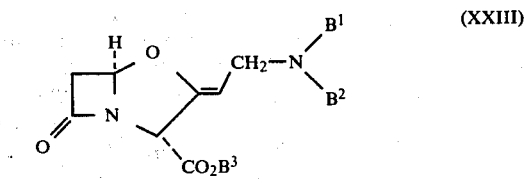

(XXIII)

wherein $B^1$, $B^2$ and $B^3$ are groups which on hydrogenation are replaced by hydrogen atoms; and thereafter recovering the crystalline zwitterionic compound of the formula (VIII) as hereinbefore described from the reaction mixture.

This process may be carried out under conditions described hereinbefore as suitable for hydrogenation of benzyl or substituted benzyl esters within formula (II).

In general catalysts containing charcoal and especially high proportions thereof are not preferred because of adsorption of the zwitterion onto the carbon.

The crystalline material may be obtained from the reaction mixture by separating the catalyst (e.g. by filtration) from the solution and thereafter gradually removing the solvent (e.g. by evaporation) until crystallisation commences and thereafter filtering off the crystals or by carefully adding a less polar solvent until crystals are obtained.

A further suitable method of obtaining good quality crystalline zwitterionic 9-aminodeoxyclavulanic acid is by recrystallisation from moisture laden acetonitrile or equivalent solvent system such as moisture laden acetone, or ethanol, isopropanol or the like.

The present invention also provides a process for the preparation of a salt of a compound of the Formula (XXIV):

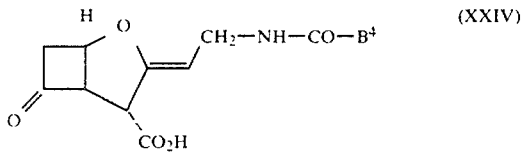

wherein $B^4$ is a group $R^9$ or $OR^9$ optionally substituted by a salted carboxyl group which process comprises the basic hydrolysis of a salt of a compound of the Formula (XXV)

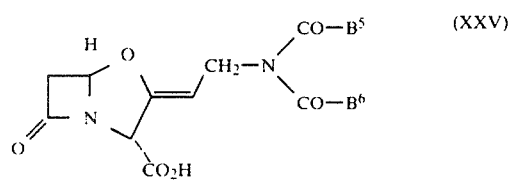

wherein $B^5$ is a group $R^9$ or $OR^9$, $R^6$ is a group $R^9$ or $B^5$ and $B^6$ are linked to form part of a cyclic moiety.

Suitably $B^4$ is a group $R^9$ optionally substituted by a salted carboxyl group.

Suitably $B^5$ is an aryl group.

Suitably $B^6$ is an aryl group.

The hydrolysis reaction is generally carried out on an aqueous solution to which base is added at such a rate as to maintain the pH in the region 7.5 to 9.8, for example at about 9.2 to 9.6. It is frequently convenient to carry out the reaction in a pH-stat.

The present invention also provides pharmaceutical compositions which comprise a compound of this invention and a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of salts of a compound of the formula (II) are particularly suitable as high tissue levels of a compound of the formula (II) can occur after administration by injection or infusion. Thus, one preferred composition aspect of this invention comprises a salt of a compound of the formula (II) in sterile form.

Unit dose compositions comprising a compound of the formula (II) or a salt of ester thereof adapted for oral administrations form a further preferred composition aspect of this invention.

The compound of the formula (II) or its salt or ester may be present in the composition as sole therapeutic agent or it may be present together witjh other therapeutic agents asuch as a β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicillin, α-sulphonyloxybenzylpenicillin, cephaloridine, caphalothin, cefazolin, cephalexin, cephacetrile, cephamadole nafate, cephapirin, cephradine, 4-hydroxy-cephalexin, cefaparole, cephaloglycine and other well known penicillins and cephalosporins or pro-drugs therefor such as hetacillin, metampicillin, 4-acetoxyampicillin, the acetoxymethyl, ethoxycarbonyloxymethyl, pivaloyloxymethyl or phthalidyl esters of benzylpenicillin or ampicillin or the phenyl or indanyl α-esters of carbenicillin or ticarcillin or the like. Such compounds are frequently used in the form of a salt or hydrate.

Naturally if the penicillin or cephalosporin present in the composition is not suitable for oral administration then the composition will be adapted for parenteral administration.

When present together with a cephalosporin or penicillin, the ratio of a compound of the formula (II) or its salt or ester present to the other antibacterial agent may vary over a wide range of ratios, for example 3:1 to 1:10 and advantageously may be from 1:1 to 1:8, for example, 1:2, 1:3, 1:4, 1:5 or 1:6.

The total quantity of compound of the formula (II) in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues and mastitis in cattle.

Normally between 50 and 1000 mg of the compounds of the invention will be administered each day of treatment but more usually between 100 and 750 mg of the compounds of the invention will be administered per day, for example as 1–6 doses, more usually 2–4 doses.

The penicillin or cephalosporin in synergistic compositions of this invention will normally be present up to or at approximately the amount at which it is conventionally used.

Particularly favoured compositions of this invention will contain from 150–1000 mg of amoxycillin, ampicillin or a pro-drug therefor and from 25–500 mg of a compound of the formula (II) or ester thereof and more suitably from 200–750 mg of amoxycillin or a salt thereof and from 50–250 mg of a compound of the formula (II).

Certain preferred compositions of this invention will contain amoxycillin trihydrate or a pharmaceutically acceptable salt of amoxycillin.

The materials present in such compositions may be hydrated if required for example ampicillin trihydrate or amoxycillin trihydrate may be employed. The weights of the antibiotics in such compositions are expressed on the basis of antibiotic theoretically available from the composition and not on the basis of the weight of pro-drug.

Highly favoured compositions of this invention are those containing the compound of the formula (VIII) in crystalline form and a penicillin or cephalosporin.

Penicillins suitable for inclusion in orally administrable compositions of this invention together with the crystalline compound of the formula (VIII) include benzylpenicillin, phenoxymethylpenicillin, propicillin, amoxycillin, ampicillin, epicillin, cyclacillin and other orally active penicillins and their salts and in-vivo hydrolysable esters and aldehyde and ketone adducts of those penicillins containing a 6-α-aminoacylamido side chain and their salts. Suitable penicillin in-vivo hydrolysable esters include the acetoxymethyl, pivaloyloxymethyl, α-ethoxycarbonyloxyethyl and phthalidyl esters of ampicillin or amoxycillin or the phenyl, tolyl and indanyl α-esters of carbenicillin and ticarcillin and salts thereof. Suitable aldehyde and ketone adducts of penicillins containing a 6-α-aminoacylamido side chain include the formaldehyde and acetone adducts metampicillin and hetacillin and their salts. Suitable penicillins for inclusion in injectably or infusably administrable compounds together with the crystalline compound of the formula (VIII) include the acceptable salts of benzylpenicillin, phenoxymethylpenicillin, carbenicillin, propicillin, ampicillin, amoxycillin, epicillin, ticarcillin, cyclacillin and other known penicillins such as pirbenicillin, azlocillin, mezlocillin or the like.

Cephalosporins suitable for inclusion in orally administrable compositions of this invention together with the crystalline compound of the formula (VIII) cephalexin, cephradine, cephaloglycine, cephaloglycine, cephaparole and their salts and other known cephalosporins and their salts and in-vivo hydrolysable esters and aldehyde and ketone adducts of those cephalosporins containing a 7-α-aminoacylamido side chain and their salts. Suitable cephalosporins for inclusion in the injectable or infusable compositions of this invention together with the crystalline compound of the formula (VIII) include the salts of cephaloridine, cephalothin, cefazolin, cephalexin, cephacetrile, cephamandole, cephapirin, cephradine, cephaloglycine, cephatrizine and other known cephalosporins.

When present in a pharmaceutical composition together with a penicillin or cephalosporin, the weight ratio of the crystlline compound of the formula (VII) present to penicillin or cephalosporin present may be as previously indicated for compounds of the formula (II).

Particularly favoured compositions of this invention will contain from 150 to 1000 mg of amoxycillin, ampicillin or an in-vivo hydrolysable ester or aldehydr or ketone adduct thereof to a salt thereof and from 50 to 500 mg of the crystalline compound of the formula (VIII); and a pharmaceutically acceptable carrier.

Highly preferred compositions will contain from 200 to 500 mg of amoxycillin or a salt thereof or ampicillin or a salt thereof. Highly preferred compositions will contain from 50 to 250 mg of the crystalline compound of the formula (VIII).

Most suitably the weight ratio of penicillin to crystalline compound of the formula (VIII) is 1:1 to 1:8, for example, 1:2 1:3, 1:4, 1:5 or 1:6. Particularly suitable ratios include 1:2, 1:3 and 1:4.

The materials present in such compositions may be hydrated. Thus in orally administrable forms, with great advantage the ampicillin may be present as ampicillin trihydrate and with even greater advantage the amoxycillin may be present as amoxycillin trihydrate.

Particularly suitable salts for use in injectable compositions containing the crystalline compound of the formula (VII) are sodium ampicillin and yet more suitably sodium amoxycillin.

The weights of the antibiotics in such compositions are expressed on the basis of pure free antibiotic equivalent present.

Certain particularly favoured oral dosage forms according to this invention include tablet or capsule formulations which contain the following approximate weights:

| Amoxycillin Trihydrate equivalent to amoxycillin | 9-Aminodeoxyclavulanic Acid |
| --- | --- |
| 250 mg | 50 |
| 250 mg | 62.5 mg |
| 250 mg | 80 mg |
| 250 mg | 125 mg |
| 250 mg | 250 mg |
| 500 mg | 62.5 mg |
| 500 mg | 100 mg |
| 500 mg | 125 mg |
| 500 mg | 165 mg |
| 500 mg | 250 mg |

Such dosage forms are generally administered three times a day.

Other favoured oral dosage forms according to this invention include tablet or capsule formulations such as those above in which the amoxycillin trihydrate is replaced by the same weight of ampicillin trihydrate. Such dosage forms are generally administered four times a day.

This invention provides a method of treating bacterial infections in humans and domestic mammals which method comprises the administration of an anti-bacterially effective amount of one of those composition hereinbefore described comprising the crystalline compound of the formula (VIII) and ampicillin or amoxycillin.

The preceding compositions may be used to treat infections of the urinary tract, respiratory tract, soft tissues and the like, for example where the infection is due to strains of *Staphylococcus aureus, Haemophilus influenzae, Escherichia coli, Klebsiella aerogenes,* Proteus spp, *Neiserria gonorrhoea* and the like. A particular use of such compositions is in the treatment of bronchitis, pneumonia and the like.

Yet other particularly suitable composition of this invention are those which contain carbenicillin, ticarcillin, or their pro-drugs. Thus certain favoured injectable compositions of this invention will contain salts of carbenicillin or ticarcillin, for example di-sodium carbenicillin or di-sodium ticarcillin, and crystalline compound of the formula (VIII). Similarly certain favoured orally administrable compositions will include a salt of an in-vivo hydrolysable ester of carbenicillin or ticarcillin, for example a sodium salt of the phenyl α-ester of carbenicillin or a sodium salt of a lower alkyl phenyl α-ester of carbenicillin or ticarcillin, and crystalline compound of the formula (VIII).

The preceding compositions may be used to treat infections of the urinary tract, for example those caused by gram negative bacteria such as *Escherichia coli, Klebsiella aerogenes,* Proteus spp, *Neisseria gonorrhoea* or *Pseudomonas aerogenosa.*

The following Examples illustrate the invention:

EXAMPLE 1

Benzyl 9-N-phthalimidodeoxyclavulanate

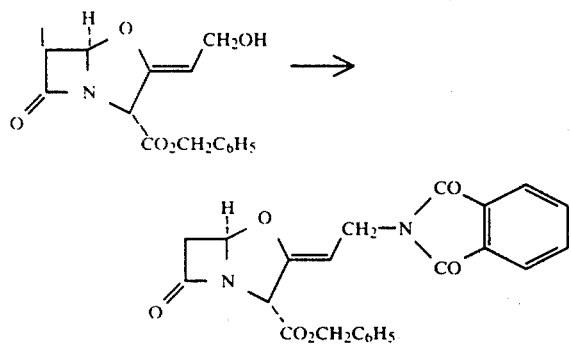

A solution of benzyl clavulanate (2.89 g), triphenylphosphine (2.8 g) and phthalimide (1.47 g) in tetrahydrofuran (50 ml) was stirred and cooled in ice-water to about 10° C. Diethyl azodicarboxylate (1.9 ml) was added rapidly with stirring. The reaction was allowed to stir during 2 hours at circa 10° C., then evaporated to a syrup under reduced pressure at ambient temperature. The syrup was diluted with ether (60 ml) and cooled to 2°–3° C. for 30 minutes. Feathery needle-like crystals had formed by the end of this time and were collected by filtration and dried in vacuo, to yield the product (2.8 g) m.p. 140° C. After washing with ethanol (25 ml) the product (1.2 g) had an improved melting point of 160° C.

I.r. (nujol mull): 1800, 1770 (w), 1735, 1715 cm$^{-1}$.

N.m.r. (CDCl$_3$);67 : 3.03 (1H, d, J17Hz, 6-$\beta$-CH), 3.42 (1H, dd, J 2.5 and 17Hz, 6-$\alpha$-CH), 4.28 (2H, d, J 7Hz, 9-CH$_2$), 4.77 (1H, t, J 7Hz, 8-CH), 5.01 (1H, s, 3-CH), 5.11 (2H, s, PhCH$_2$), 5.67 (1H, d, J 2.5Hz, 5-CH), 7.23 (5H, s, Ph), 7.6–7.9 (4H, m, C$_6$H$_4$).

The corresponding p-methoxybenzyl, methyl and methoxymethyl esters may be prepared by replacing benzyl clavulanate by p-methoxybenzyl clavulanate, methyl clavulanate or methoxymethyl clavulanate.

EXAMPLE 2

Lithium 9-N-phthalimidodeoxyclavulanate

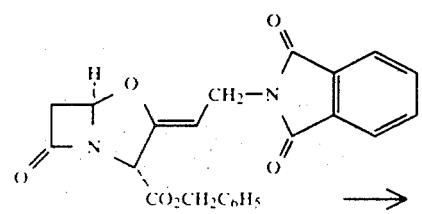

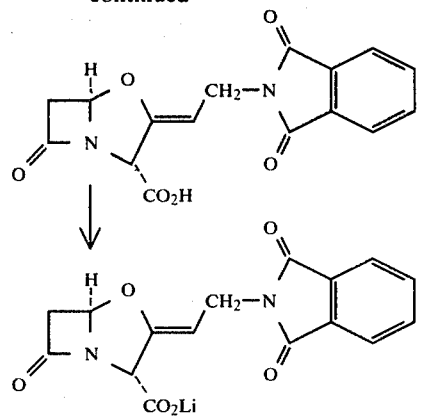

Benzyl 9-N-phthalimidodeoxyclavulanate (1.0 g) in redistilled tetrahydrofuran (40 ml) containing water (0.05 ml) was hydrogenated over 10% palladised charcoal (Engelhard 4504) at ambient temperature and pressure for 30 minutes. (At this time, tlc showed the presence of a little unreduced starting ester). The catalyst was removed by filtration, the filtrate poured into water (150 ml) and titrated to pH 7.0 by the addition of 1.0M lithium hydroxide solution. The unreacted starting material was filtered off, and washed with a little water. The filtrate and washings were evaporated in vacuo at ambient temperature to a white crystalline solid, which was triturated with acetone (30 ml), filtered off, washed with acetone (10 ml), dichloromethane (10 ml) and finally with ether (10 ml), to yield the product, (0.5 g). (There was 0.2 g recovered starting ester).

I.r. (nujol mull): 1785, 1765 (w), 1705, 1630, 1610 cm$^{-1}$.

N.m.r. (D$_2$O; D.S.S. ref.)$\delta$: 3.0 (1H, d, J 17Hz, 6-$\beta$-CH), 3.53 (1H, dd, J 17 and 2.5Hz, 6-$\alpha$-CH), 4.26 (2H, d, J 6.5Hz, 9-CH$_2$) (8-CH partially obscured by HOD), 4.90 (1H, s, 3-CH), 5.70 (1H, d, J 2.5Hz, 5-CH), 7.74 (4H, s, C$_6$H$_4$). It is possible that this product is a crystalline hydrate).

Corresponding sodium, potassium and calcium salts may also be prepared in this manner.

EXAMPLE 3

Benzyl 9-N-succinimidodeoxyclavulanate

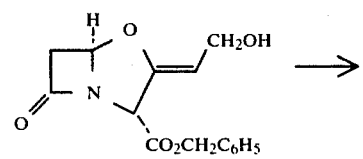

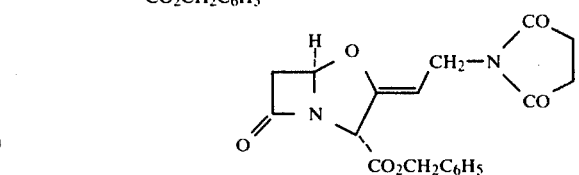

To a stirred solution of benzyl clavulanate (2.89 g), triphenylphosphine (3.14 g) and succinimide (0.99 g) in redistilled tetrahydrofuran (50 ml) at 5° C. was added diethyl azodicarboxylate (2.1 ml). The red solution was stirred for 1 hour, allowing the temperature to rise to ambient. The solvent was evaporated, and cyclohexane-ethyl acetate (3:2, 30 ml) added. The insoluble material was filtered off, washed with a little of the same solvent. The filtrate was evaporated under reduced pressure, and the residue subjected to column chromatography on silica gel using cyclohexane - ethyl acetate (3:2) graded to 1:2 ratio. After the diene had eluted, fractions containing the required compound (detected by tlc, 0.02M KMnO₄ spray) were collected, combined and evaporated under reduced pressure (2.6 g total residue). This material partly solidified. It was triturated with CCl₄ (10 ml), cooled to −5° C., filtered off the insoluble material (Ph₃P→O) and the filtrate evaporated to a yellow oil (1 g). This still contained some triphenylphosphine oxide (circa 20%) by n.m.r.

I.r. (1/f): 1800, 1745, 1700 cm$^{-1}$.

N.m.r. (CCl₄)δ: 2.53 (4H, s, CH$_2$CH$_2$), 3.05 (1H, d, J 17Hz, 6-β-CH), 3.50 (1H, dd, J 2.5 and 17Hz, 6-α-CH), 4.10 (2H, d, J 7Hz, 9-CH$_2$), 4.68 (1H, t, J 7Hz, 8-CH), 4.97 (1H, s, 3-CH), 5.16 (2H s, PhCH$_2$), 5.68 (1H, d, J 2.5Hz, 5-CH) and 7.33 (5H, s, C$_6$H$_5$).

EXAMPLE 4

Lithium 9-N-succinimidodeoxyclavulanate

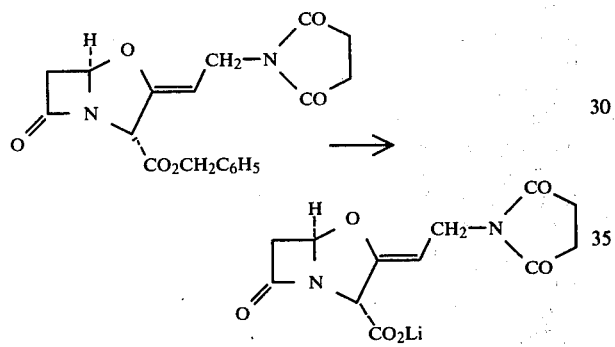

Benzyl N-succinimidodeoxyclavulanate (1.2 g, containing some triphenylphosphine oxide) in tetrahydrofuran (60 ml) was hydrogenated at room temperature and pressure over 10% palladised charcoal (0.6 g) for 20 minutes. The catalyst was filtered off and replaced with a further 0.6 g of fresh catalyst, and the hydrogenation continued for a further 20 minutes. The reaction was not complete, by tlc, but it was then worked up to avoid decomposition. The catalyst was filtered off, and the filtrate diluted with water (150 ml). The solution was tirtrated to pH 7.3 with 1M lithium hydroxide solution. The tetrahydrofuran was evaporated under reduced pressure, and the aqueous solution extracted with 2×100 ml portions of ethyl acetate. (These extracts were combined, dried over Na$_2$SO$_4$ and evaporated to recover some starting material, contaminated with most of the Ph₃P→O). The aqueous layer was evaporated to dryness in vacuo at ambient temperature. The residue was triturated with acetone (75 ml) and the resulting crystalline solid filtered off, washed with acetone and with ether, and air-dried, to yield the product (0.19 g).

I.r. (nujol mull): 1785, 1695, 1615 cm$^{-1}$.

N.m.r. (D$_2$O, CH$_3$CN=2.0 reference )δ: 2.67 (4H, s, CH$_2$CH$_2$), 2.99 (1H, d, J 17Hz, 6-β-CH), 3.54 (1H, dd, J 17 and 2.5Hz, 6-α-CH), 4.09 (2H, d, J 7Hz, 9-CH$_2$), (8-CH obscured by HOD peak at circa δ 4.6), 4.82 (1H, s, 3-CH), and 5.66 (1H, d, J 2.5Hz, 5-CH).

EXAMPLE 5

Benzyl 9-(N-benzyloxycarbonyl-N-benzoyl)aminodeoxyclavulanate

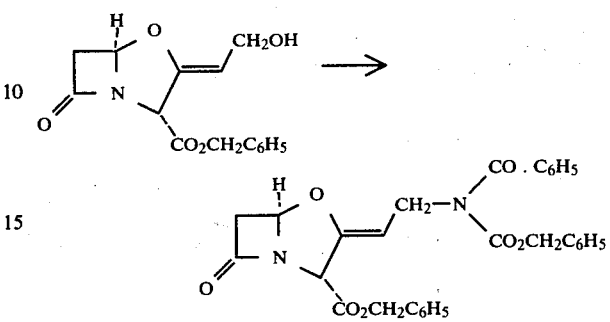

To a solution of benzyl clavulanate (2.89 g), benzyl N-benzoylcarbamate (2.55 g) and triphenyl phosphine (3.14 g) in tetrahydrofuran (50 ml), stirred and cooled to 5° C., was added diethyl azodicarboxlate (2.1 ml). Immediately afterwards, thin layer chromatography showed that no starting material remained. The solvent was removed by evaporation under reduced pressure, and the residue triturated with a mixture of ethyl acetate (20 ml) and cyclohexane (30 ml). The insoluble materials were discarded, the filtrate evaporated to a gum, and subjected to careful reverse gradient elution chromatography on silica gel, using ethyl acetate and cyclohexane as eluents, graded from 3:1 to 4:1 ratio of cyclohexane to ethyl acetate. The product eluted after the diene and a small amount of a non β-lactam containing product. Fractions containing the product (by thin layer chromatography) were combined and evaporated to an oil (1.4 g); there was also obtained 0.4 g of slightly less pure material.

I.r. (film): 1808, 1748, 1690 (sh), 1682 cm$^{-1}$;

N.m.r. (CDCl$_3$)δ: 2.89 (1 H, d, J 17 Hz, 6-β-CH), 3.36 (1 H, dd, J .17 and 3 Hz, 6-α-CH), 4.47 (2 H, d, J 7 Hz, 9-CH$_2$), 4.86 (1 H, t, J 7 Hz, 8-CH), 4.92 (2 H, s, carbamate CH$_2$Ph), 5.01 (1 H, bs, 3-CH), 5.10 (2 H, s, ester CH$_2$Ph), 5.54 (1 H, d, J 3 Hz, 5—CH), and 6.80–7.50 (15 H, 3×C$_6$H$_5$).

EXAMPLE 6

Lithium 9-N-benzoylaminodeoxyclavulanate

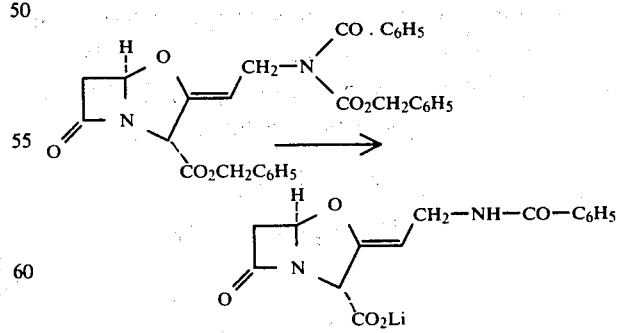

The ester of Example 5 (0.88 g) in redistilled tetrahydrofuran (75 ml) containing water (0.2 ml) was hydrogenated over 10% palladised charcoal (0.44 g) at ambient temperature and pressure for 20 minutes. The catalyst was removed by filtration, the filtrate diluted with water (125 ml) and titrated to pH 7.2 by the addition of 1 M aqueous lithium hydroxide solution. The solution was evaporated under reduced pressure until ca 2 ml remained, and this residue was treated with acetone (50 ml). The product crystallised, and it was collected by filtration, washed with acetone (20 ml) and with ether (20 ml) and allowed to dry in air. There was obtained 0.4 g of the named product as fine colourless needles.

I.r. spectrum (nujol mull): 3300 (br, with sharp peak), 1788, 1708, 1630, 1615 cm$^{-1}$.

N.m.r. (D$_2$O)δ: 2.86 (1 H, d, J 17 Hz, 6-βCH), 3.34 (1 H, dd, J 17 Hz and 3 Hz, 6-α-CH), 3.83 (2 H, d, J 8 Hz, 9-CH$_2$), 4.68 (1 H, t, J 8 Hz, 8-CH), 4.75 (1 H, bs, 3-CH), 5.52 (1 H, d, J 3 Hz, 5-CH), 7.15–7.65 (5 H, m, COC$_6$H$_5$).

EXAMPLE 7

Benzyl N,N-dibenzyloxycarbonylaminodeoxyclavulanate

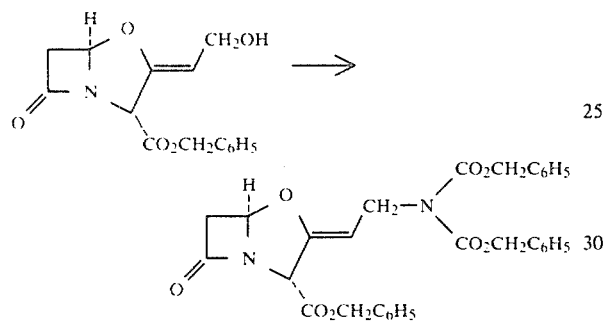

To a solution of benzyl clavulanate (2.89 g), triphenylphosphine (3.1 g) and benzyl N-benzyloxycarbonylcarbamate (2.85 g) in tetrahydrofuran (50 ml), stirred at 5° C., was added diethylazodicarboxylate (2.1 ml). Thin layer chromatography (3:1 cyclohexane-ethyl acetate) showed that all the starting material had been consumed. After 20 minutes, the tetrahydrofuran was evaporated under reduced pressure, and a mixture of ethyl acetate and cyclohexane (2:3, 50 ml) was added to the residue. After cooling for a short time, the precipitated diethyl hydrazodicarboxylate (1.2 g) was filtered off and washed with a little of the same solvent. The filtrate was re-evaporated, and the residue subjected to reverse gradient chromatography on silica gel, using ethyl acetate and cyclohexane graded from 1:3 to 1:4 ratio. A middle cut was taken, containing (by thin layer chromatography) some diene, the product, some starting imide and other compounds. These fractions were combined and evaporated to dryness. The residue was treated with carbon tetrachloride (20 ml), and the crystalline starting imide (1.3 g) filtered off. The filtrate was evaporated and the residue rechromatographed on the same solvent system. The product eluted last, and fractions containing it were combined, evaporated to dryness and dried under high vacuo, to yield 0.6 g of pure material and a further 0.4 g of slightly impure material.

I.r. (1/f) 1802 (β-lactam C=O), 1752, sh 1730, 1700 cm$^{-1}$.

N.m.r.: (CDCl$_3$)δ:2.77 (1 H, d, J 17 Hz, 6-β-CH), 3.28 (1 H, dd, J 2.5 and 17 Hz, 6-α-CH), 4.37 (2 H, d, J 7 Hz, 9-CH$_2$), 4.69 (1 H, t, J 7 Hz, 8-CH), 4.94 (1 H, s, 3-CH), 5.09 (2 H, s, 3-CO$_2$CH$_2$Ph), 5.16 (4 H, s, N(CO$_2$CH$_2$Ph)$_2$), 5.36 (1 H d, J 2.5 Hz, 5-CH), 7.25 (15 H, s, 3 × C$_6$H$_5$).

The intermediates were prepared as follows:

A suspension of benzyl carbamate (42 g) in 1,2-dichloroethane (280 ml) was stirred and cooled in ice, A solution of oxalyl chloride (50 g) in dichloroethane (60 ml) was added. The mixture was heated under reflux, which was maintained for 18 hours. The mixture was cooled, and the suspended insoluble matter, (PhCH$_2$OCONHCO—)$_2$, m.p. 246° C., 2.2 g, filtered off. The solution was distilled, initially at atmospheric pressure, and then at 10 mm pressure. Benzyloxycarbonyl isocyanate (11.2 g) then distilled at 110°–117° C. To a solution of benzyl alcohol (20 g) in dichloromethane (70 ml) was added freshly distilled benzyloxycarbonyl isocyanate (8.7 g). After the vigorous reaction has subsided, the solvent was removed under reduced pressure, and the residue triturated with ether and petroleum ether b.p. 30°–40° (1:1, 100 ml). The product was collected by filtration to yield 11.0 g, m.p. 108° (corr.).

In analogous manner to the preceding preparation of benzyl N,N-dibenzyloxycarbonylaminodeoxyclavulanate, the following compounds may be prepared: p-methoxybenzyl N,N-dibenzyloxycarbonylaminodeoxyclavulanate, p-nitrobenzyl N,N-dibenzyloxycarbonylaminodeoxyclavulanate, p-bromobenzyl N,N-dibenzyloxycarbonylaminodeoxyclavulanate, methyl N,N-dibenzyloxycarbonylaminodeoxyclavulanate.

EXAMPLE 8

9-Aminodeoxyclavulanic Acid

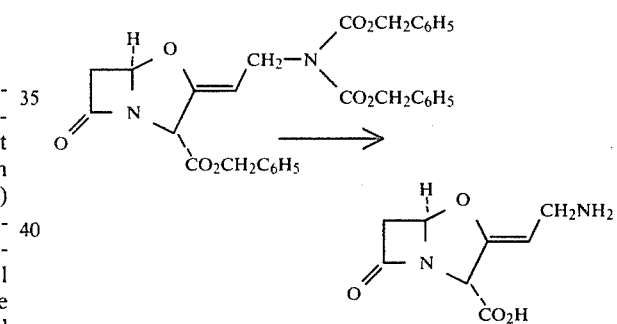

A solution of benzyl N,N-dibenzyloxycarbonylaminodeoxyclavulanate (0.9 g) in tetrahydrofuran (15 ml), ethanol (15 ml) and water (12 ml) was hydrogenated for 40 minutes at ambient temperature and pressure over 10% palladised barium sulphate (0.5 g), at which time thin layer chromatography (CHCl$_3$:EtOH:CH$_3$COOH 7:7:1) showed the absence of starting material and materials at intermediate stages of reduction. The catalyst was removed by filtration, and washed with a little water. The filtrate and washings were evaporated in vacuo at circa 5° C. to about 0.7 ml. Scratching of this syrup induced crystallisation. Most of the remaining water was removed by slow vacuum evaporation, to leave a pasty mass of crystals (0.35 g). This was triturated with anhydrous ethanol (5 ml), filtered off, washed with ethanol (5 ml), acetone (1 ml) and ether (5 ml), and dried in air at ambient temperature, to yield 0.22 g of pale buff crystalline solid. Reworking of mother liquors, flask residues etc. afforded a further 0.03 g. Recrystallisation of a small sample from aqueous acetonitrile afforded colourless feathery needles. I.r. (nujol mull): very broad absorption with some structure 3680–2100 cm$^{-1}$ (—N$^+$H$_3$, —CO$_2^-$), 2180

(br, w, N⁺H₃), 1803 (β-lactam C=O), 1695 (C=C), 1640, 1625, 1585 (CO₂⁻).

D₂O (CH₃CN ref=2.0) δ3.08 (1 H, d, J 17 Hz, 6-β-C$\underline{H}$), 3.54 (1 H, dd, J 17 and 2.5 Hz, 6-α-C$\underline{H}$), 3.63 (2 H, d, J 8 Hz, 9-C$\underline{H}_2$), 4.81 (1 H, t, J 8 Hz, partially obscured by HOD peak at 4.64), 4.96 (1 H, s, 3-C$\underline{H}$), 4.74 (1 H, d, J 2.5 Hz, 5-C$\underline{H}$).

Some properties and Pharmacology of 9-aminodeoxyclavulanic acid [9-ADCA]

a. Crystalline zwitterionic 9-aminodeoxyclavulanic acid appears to possess enhanced storage stability as compared to salts of clavulanic acid such as the sodium salt, for example highly pure crystalline 9-aminodeoxyclavulanic acid left in moist air did not noticeably change colour over the same period that sodium clavulanate visibly darkened.

b. Crystalline zwitterionic 9-aminodeoxyclavulanic acid dissolves readily in sterile water to form an injectable composition, for example a 10–30% w/w solution may be prepared, furthermore such solutions are of an approximately neutral pH so that no irritant effects due to pH extremes occur.

c. When administered to mice the following blood levels occurred:

| Mouse Blood Levels of 9-ADCA following administration to mice - 20 mg/kg sub-cutaneous | | | | | |
|---|---|---|---|---|---|
| | Time in Minutes | | | | |
| | 10 | 20 | 30 | 45 | 60 |
| 9-ADCA | 16.13 | 12.8 | 9.9 | 5.2 | 2.03 |
| Sodium clavulanate | 9.39 | 8.7 | 3.0 | 2.0 | 0.5 |

| Mouse Blood Levels of 9-ADCA following p/o administration to mice - 20 mg/kg orally. | | | | | |
|---|---|---|---|---|---|
| | Time in Minutes | | | | |
| | 15 | 30 | 45 | 60 | 90 |
| 9-ADCA | 4.98 | 5.34 | 3.19 | 1.98 | 1.46 |
| Sodium clavulanate | 4.4 | 2.9 | 2.5 | 0.85 | 0.3 | d. When administered to mice at 20 mg/kg subcutaneously, urinary recovery, 0-4 hours, of 9-ADCA was approximately 30-40%. When administered to mice at 20 mg/kg orally, urinary recovery, 0-4 hours, of 9-ADCA was approximately 13-16%.

e. When administered to mice suffering from a peritoneal infection due to E. coli JT 39 the following results were obtained:

| Oral administration (Dosed 1, 3 and 5 hours post infection) | |
|---|---|
| Amoxycillin alone | >100 mg/kg × 3 |
| Amoxycillin + 10 mg/kg sodium clavulanate | 23 mg/kg × 3 |
| Amoxycillin + 10 mg/kg 9-ADCA | 12 mg/kg × 3 |
| 9-ADCA alone | >20 mg/kg × 3 |

| Sub-cutaneous administration (Dosed 1 and 5 hours post infection) | |
|---|---|
| Amoxycillin alone | >100 mg/kg × 2 |
| Amoxycillin + 2 mg/kg sodium clavulanate | 11 mg/kg × 2 |
| Amoxycillin + 2 mg/kg 9-ADCA | 6 mg/kg × 2 |
| 9-ADCA alone | >5 mg/kg × 2 |

EXAMPLE 9

Benzyl 9-(N-benzyloxycarbonyl-N-methoxycarbonyl)aminodeoxyclavulanate

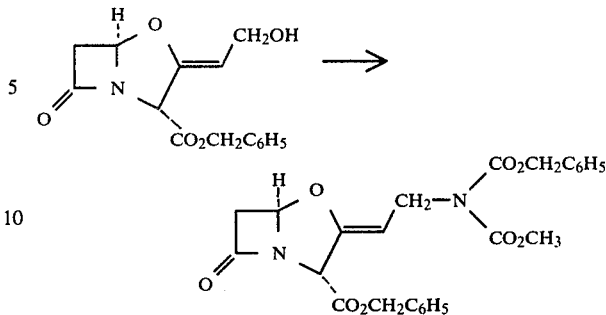

To a solution of benzyl clavulanate (3.9 g), triphenyl phosphine (4.3 g) and methyl N-benzyloxycarbonylcarbamate (2.83 g) in tetrahydrofuran (70 ml) cooled and stirred at 5° C., was added diethyl azodicarboxylate (2.8 ml). After 30 minutes the solvent was evaporated and 3:2 cyclohexane-ethylacetate (70 ml) added. The insoluble material was filtered off, and the filtrate re-evaporated to dryness. The residue was subjected to column chromatography on silica gel using 3:1 cyclohexane and ethyl acetate as eluents. A middle cut was taken between the diene and benzyl clavulanate, and this was then rechromatographed using the same solvent system. The fractions containing the pure product (by i.r. spectra and thin layer chromatography) were collected and combined, to yield 0.9 g of the desired product.

I.r. (film)νmax: 1810, 1870–1700 (br with fine structure).

N.m.r. (CDCl₃)δ: 2.85 (1 H, d, J 17 Hz, 6-β-C$\underline{H}$), 3.34 (1 H, dd, J 17 and 2.5 Hz, 6-α-CH), 3.73 (3H, s, OCH₃), 4.33 (2 H, d, J 7 Hz, 9-C$\underline{H}_2$), 4.67 (1 H, t, J 7 Hz, 8-C$\underline{H}_2$), 4.96 (1 H, bs, 3-C$\underline{H}$), 5.10 and 5.14 (4 H, 2 s, 2×C$\underline{H}_2$C₆H₅), 5.46 (1 H, d, J 2.5 Hz, 5-C$\underline{H}$), 7.25 (10 H, bs, 2×C₆$\underline{H}_5$).

EXAMPLE 10

Lithium 9-N-methoxycarbonylaminodeoxyclavulanate

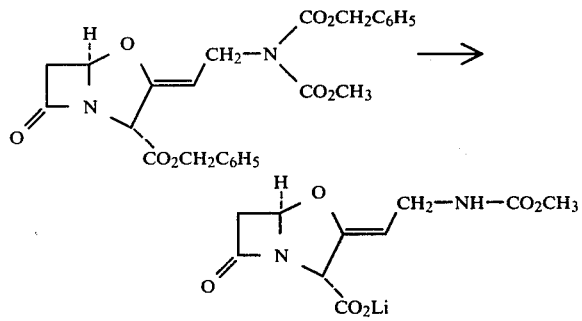

A solution of benzyl N-benzyloxycarbonyl-9-N-methoxycarbonylaminodeoxyclavulanate (1.0 g) in tetrahydrofuran (60 ml) and water (0.1 ml) was hydrogenated over 10% palladised charcoal (0.6 g) for 20 minutes, by which time thin layer chromatography showed that no benzyl ester remained. The catalyst was removed by filtration, the filtrate diluted with water (60 ml) and tritrated to pH 7.2 with 1 M aqueous lithium hydroxide solution. The slightly yellow solution was treated with pre-washed decolourising charcoal (0.3 g) which was also filtered off. The filtrate was evaporated in vacuo to low volume (circa 1 ml). Acetone (20 ml)

was added, and the colourless solid which was precipitated was filtered off, washed with acetone (5 ml) and with ether (5 ml) and dried in air, to yield 0.3 g of product.

I.r. (nujol mull) νmax: 3360 (br, with sharp peak), 1780, 1735, 1710 (br), 1625 (br) cm$^{-1}$.

N.m.r. (D$_2$O)δ: 3.03 (1 H, d, J 17 Hz, 6-β-CH), 3.61 (1 H, dd, J 17 and 2.5 Hz, 6-α-CH), 3.59 (3 H, s, OCH$_3$), 3.74 (2 H, d, J 7 Hz, 9-CH$_2$), 4.60 (HOD), 4.73 (1 H, t, J 7 Hz, 8-CH), 4.85 (1 H, bs, 3-CH), 5.68 (1 H, d, J 2.5 Hz, 5-CH).

EXAMPLE 11

Benzyl 9-(1-methyl-2,4,5-trioxoimidazolid-3-yl)deoxyclavulanate

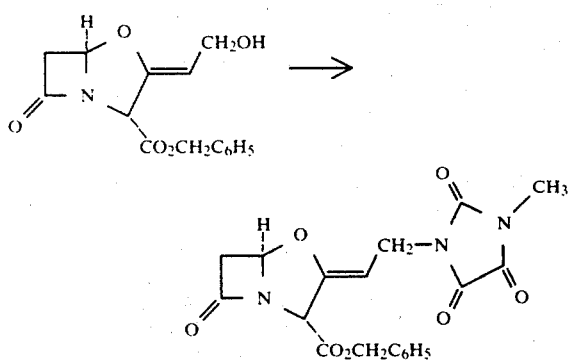

To a solution of benzyl clavulanate (2.89 g), triphenyl phosphine (3.14 g) and 1-methylimidazolidine-2,4,5-trione (N-methylparabanic acid, 1.28 g) in tetrahydrofuran (50 ml), stirred and cooled to circa 5° C., was added diethylazodicarboxylate (2.1 ml). After 30 minutes the mixture was evaporated to dryness and 3:2 cyclohexane-ethyl acetate (50 ml) added. The insoluble material was filtered off. The filtrate was re-evaporated, and subjected to gradient elution chromatography on silica gel using cyclohexane and ethyl acetate (graded from 3:2 to 2:3 ratio) as eluents. The product eluted between the diene and a trace of unreacted benzyl clavulanate. It was isolated as a pale yellow oil (1.3 g).

I.r. (liquid film) νmax: 1805, 1760–1730 (br) cm$^{-1}$;

N.m.r. (CDCl$_3$)δ: 3.07 (1H, d, J 17 Hz, 6-β-CH), 3.16 (3 H, s, N-CH$_3$), 3.55 (1H, dd, J 17 Hz and 3 Hz, 6-α-CH), 4.30 (2H, d, J 7 Hz, 9-CH$_2$), 4.76 (1H, bt, J 7 Hz, 8-CH), 5.07 (1H, bs, 3- CH), 5.19 (2H, s CH$_2$C$_6$H$_5$), 5.73 (1H, bd, J 3 Hz, 5-CH), 7.35 (5H, bs, CH$_2$C$_6$H$_5$).

EXAMPLE 12

Benzyl 9-(4-methyl-3,5-dioxo-1,2,4-oxadiazolidin-2-yl)-deoxyclavulanate

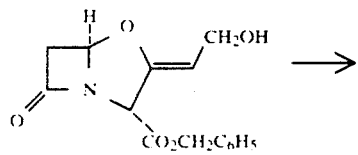

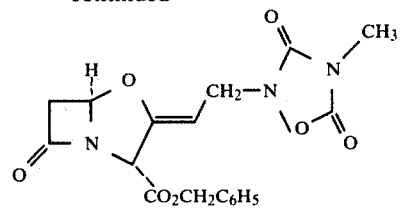

To a solution of benzyl clavulanate (250 mg), triphenyl phosphine (270 mg) and 4-methyl-1,2,4-oxadiazolidine-3,5-dione (100 mg) in tetrahydrofuran (7 ml), cooled to circa 5° C. and stirred, was added diethyl azodicarboxylate (0.18 ml). After 40 minutes the solvent was evaporated, 3:2 cyclohexane-ethyl acetate (20 ml) added, and the insoluble material filtered off. The filtrate was evaporated to dryness, and the residue subjected to column chromotography on silica gel, eluting with cyclohexane and ethyl acetate graded from 3:1 ratio to pure ethyl acetate. The product eluted between the diene and some unreacted benzyl clavulanate. Fractions containing it (by thin layer chromatography) were combined and evaporated to yield 140 mg of the required product as a pale yellow oil.

I.r. νmax: 1805, 1760–1738 (br), 1750 (sh) cm$^{-1}$.

N.m.r. (CDCl$_3$)δ: 3.04 (3H, s, N-CH$_3$), 3.05 (1H, d, J 17 Hz, 6-β-CH), 3.46 (1H, dd, J 17 Hz and 3 Hz, 6-α-CH), 4.2–4.4 (2H, AA'X, J 6 and 9 Hz, 9-CH$_2$), 4.70 (1H, dt, J 7 and 7 Hz, 8-CH), 5.06 (1H, s, 3-CH), 5.14 (2H, s, CH$_2$C$_6$H$_5$), 5.66 (1H, d J 3 Hz, 5-CH), and 7.29 (5H, s, CH$_2$C$_6$H$_5$).

EXAMPLE 13

Benzyl 9-N-p-toluenesulphonyloxy-N-benzyloxycarbonylaminodeoxyclavulanate

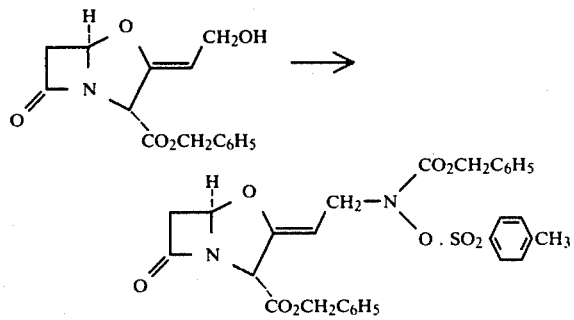

Benzyl clavulanate (2.89 g), benzyl N-p-toluene-sulphonyloxycarbamate (3.22 g) and triphenylphosphine (3.14 g) were dissolved in dry tetrahydrofuran (50 ml). The solution was stirred and cooled to 5° C. Diethyl azodicarboxylate (2.1 ml) was added dropwise. After 20 minutes the solvent was evaporated under reduced pressure, and ethyl acetate-cyclohexane (2:3, 50 ml) added. After cooling at 5° C. for 30 minutes, the insoluble material was filtered off, and washed with a few ml of the same solvent mixture. The filtrate was re-evaporated to a syrup, which was subjected to gradient elution chromatography on silica gel using ethyl acetate and cyclohexane graded from 1:3 ratio to 1:1. The title compound was eluted after a little diene. Fractions containing it (by thin layer chromatography) were combined and evaporated to an oil (3g). This was sufficiently pure for further reaction.

I.r. (film), νmax: 1810, 1740 - 1760, 1700 (sh), 1603 cm$^{-1}$.

N.m.r. (CDCl$_3$) δ 2.35 (3H, s, C$_6$H$_4$CH$_3$), 3.02 (1H, d, J 17 Hz, 6-β-CH), 3.39 (1H, dd, J 17 Hz and 3Hz, 6-α-CH), 4.2–4.4 (2H, m, 9-CH$_2$), 4.74 (1H, t, J 7 Hz, 8-CH), 4.83 (2H, s, CH$_2$C$_6$H$_5$), 5.05 (1H, s, 3-CH), 5.11 (2H, s, C$_6$H$_5$CH$_2$), 5.58 (1H, d, J 3 Hz, 5-CH), 7.28 (10H, bs, (C$_6$H$_5$)$_2$), 7.17 and 7.61 (4H, A$_2$B$_2$q, J 8 Hz, C$_6$H$_4$).

The intermediate benzyl N-p-toluenesulphonyloxycarbamate was prepared by the reaction of benzyl-N-hydroxycarbamate with toluenesulphonyl chloride in dry ether containing triethylamine. The compound was isolated as a colourless solid, m.p. 115° C. (dec.).

Analysis: Theory: C 56.1; H 4.71; N 4.36; S 9.96%; Found: C 56.2; H 4.84; N 4.23; S 10.1%.

Example 14

9-Aminodeoxyclavulanic acid p-tolunesulphonate salt

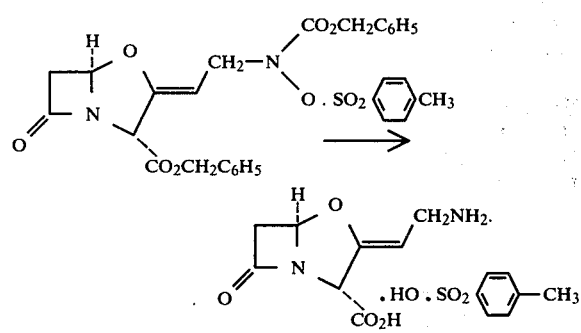

Hydrogenation of the product of Example 13 in dilute solution in tetrahydrofuran using palladised charcoal as catalyst gives a solution of the p-toluene-sulphonate salt of 9-aminodeoxyclavulanic acid. Removal of the solvent by evaporation followed by trituration with acetone and then ether afforded the title compound in poor yield in solid form.

I.r. (nujol mull): ν max 2600–3600 (broad, NH$_3^{30}$), 1805 (β-lactam C=O), 1730 (COOH) cm$^{-1}$.

N.m.r.: no benzylic protons.

The title compound gives a very acidic solution in water. The presence of an excess of a resin such as IR 45 (OH) or Amberlyst stabilises the solution by absorption of the toluenesulphonic acid.

EXAMPLE 15

Benzyl 9-(N-benzyloxycarbonyloxy-N-benzyloxycarbonyl)-aminodeoxyclavulanate

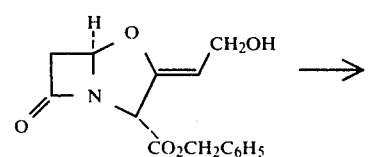

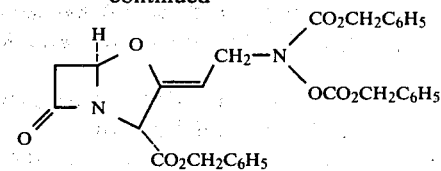

Benzyl clavulanate (2.89 g), triphenylphosphine (3.14 g) and N,O-bisbenzyloxycarbonylhydroxylamine (3.01 g) were dissolved in tetrahydrofuran (50 ml) and stirred at 5° C. Diethyl azodicarboxylate (2.1 ml) was added slowly, and the solution stirred for 30 minutes. The reaction was evaporated to dryness in vacuo, and a mixture of ethyl acetate (20 ml) and cyclohexane (30 ml) added. The insoluble material was filtered off and discarded. The filtrate was evaporated to dryness in vacuo and the residue submitted to gradient elution chromatography on silica gel using ethyl acetate and cyclohexane as eluents, graded from 1:3 to 1:1 ratio. The compound eluted after a small quantity of the diene. Fractions containing it (by thin layer chromotography) were combined and evaporated to dryness in vacuo, to yield 0.8 g of the title product as an oil.

I.r. (film) ν max 1795 (broad), 1740 (broad) cm$^{-1}$.

N.m.r. (CDCl$_3$) δ 2.85 (1H, d, J 17 Hz, 6-β-CH), 3.30 (1H, dd, J 17 and 3 Hz, 6-α-CH), 4.27 (2H, d, J 7 Hz, 9-CH$_2$), 4.74 (1H, t, J 7 Hz, 8-CH), 4.98 (1H, s, 3CH), 5.09 (2H, s, CH$_2$C$_6$H$_5$, 5.10 (2H, s, CH$_2$C$_6$H$_5$), 5.16 (2H, s, CH$_2$C$_6$H$_5$), 5.47 (1H, d, J 3 Hz, 5-CH), and 7.25 (15H, broad s, (CH$_2$C$_6$H$_5$)$_3$).

The N,O-bisbenzyloxycarbonylhydroxylamine was prepared by the reaction of benzyl N-hydroxycarbamate (4.6 g) with benzyl chloroformate (4.7 g) in dry ether (100 ml) at 0° C.; triethylamine (3.85 ml) was then added dropwise. After 30 minutes the triethylamine hydrochloride was removed by filtration, washed with ether, and the filtrate evaporated in vacuo to a colourless oil which later solidified. It was triturated with petroleum ether b.pt. 40°–60° C., filtered off and dried in vacuo, to yield the product, 5.5 g. as a rather unstable colourless crystalline solid.

I.r. (nujol mull) νmax 3240 (NH), 1815 (C=O), 1750 (sh), 1725 (ester C=O) cm$^{-1}$.

EXAMPLE 16

Benzyl 9-(N-phenoxycarbonyl)benzyloxycarbonylaminodeoxyclavulanate

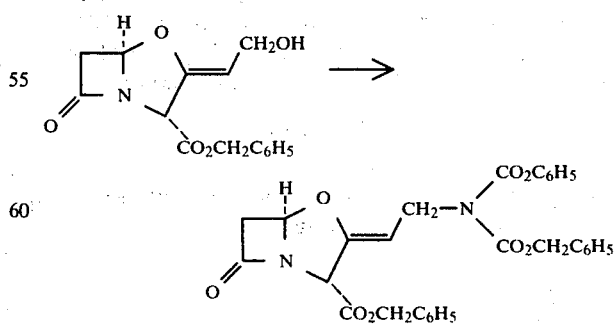

To a cooled (ca. 5° C.) stirred solution of benzyl clavulanate (2.0 g), triphenylphosphine (2.17 g) and phenyl N-benzyloxycarbamate (1.88 g) in tetrahydrofuran (redistilled, 40 ml) was added diethyl azodicarboxylate (1.5 ml), and the solution stirred, warming slowly to ambient temperature, during 3 hr. The solvents were removed in vacuo, and the residue stored at −20° C. overnight. The residue was triturated with 30 ml of 1:2 ethyl acetate - cyclohexane. About 10 ml of the solvent was evaporated in vacuo without the application of heat. The remainder was filtered cold, and the insolubles washed with a little of the 1:2 solvent mixture. The filtrate was evaporated in vacuo, and the residue subjected to column chromatography on silica gel using ethyl acetate-cyclohexane (1:3) as elution solvent, monitoring fractions by tlc using 9:2 cyclopentane - methyl acetate, a band of compounds of Rf about 0.4 was collected. This was combined, and subjected to reverse gradient elution on silica gel using cyclohexane and ethyl acetate graded from 3:1 to 4:1 ratio. The most polar component was collected. It was separated from a slightly less polar component. Fractions containing the required compound were collected and evaporated to an oil, under reduced pressure; yield 0.2 g. It had Ir (film) 1805, 1738 cm$^{-1}$ (broad, with sh. at ca. 1700 cm$^{-1}$); nmr (CDCL$_3$) 2.80 (1H, d, J 17 Hz, 6-β-C$\underline{H}$), 3.33 (1H, dd, J 17 and 3Hz, 6-α-C$\underline{H}$), 4.49 (2H, d, J 7Hz, 9-C$\underline{H}_2$), 4.82 (1H, t, J 7Hz, 8-C$\underline{H}$), 5.03 (1H, s, 3-C$\underline{H}$), 5.14, 5.24 (2×2H, 2s, 2×PhC$\underline{H}_2$) 5.50 (1H, d, J 3Hz, 5—C$\underline{H}$), 6.9-7.5 (15H, m, C$_6$$\underline{H}_5$ and 2×C$_6$ $\underline{H}_5$CH$_2$).

EXAMPLE 17

Benzyl N$_1$N-dibenzyloxycarbonylaminodeoxyclavulanate

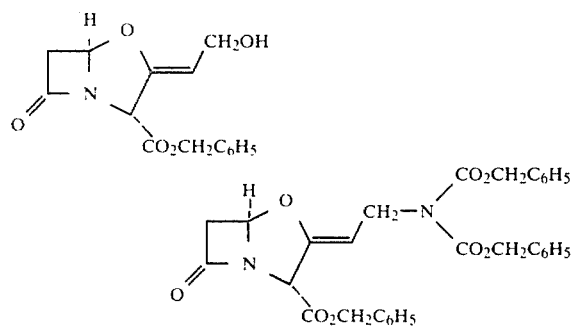

To a solution of benzyl clavulanate (2.89g) triphenylphosphine (3.14 g) and bis benzyloxycarbonylimide (2.84 g) in benzene (59 ml) cooled and stirred at 5° C. was added diethyl azodicarboxylate (2.1ml). After 45 mins. the solution was filtered to remove diethyl hydroazodicarboxylate (1.8 g) and the filtrate evaporated under reduced pressure. The residue was subjected to column chromatography on silica gel, using ethyl acetate and cyclohexane as eluents graded from 1:2 to 1:3 ratio. Fractions containing the product (by t.l.c.) were combined and evaporated. Unreacted imide was removed from these fractions by trituration with carbon tetrachloride petrol ether 40°/60°; the crystalline imide was removed by filtration and the filtrate re-evaporated to give a total of 2.35 g of pure product (with i.r. identical to authentic material of Example 7).

EXAMPLE 18

Di-sodium 9-phthalamidodeoxyclavulanic acid

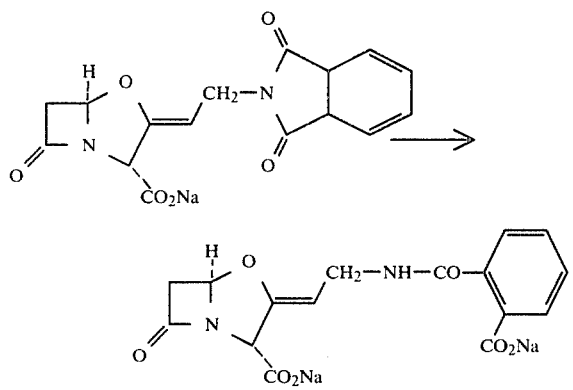

9-Phthalimidodeoxyclavulanic acid sodium salt (from the hydrogenation of 3 g benzyl ester and neutralization with NaOH solution) was hydrolyzed on a pH-Stat with 2 M sodium hydroxide solution at pH 9.5 until uptake became slow (required 3.4 ml; theory 3.6 ml). The yellow solution was evaporated to a foam which was triturated with acetone (50 ml) . The sodium salt (3.2 g) was filtered off, washed with ether and dried in vacuo. This was dissolved in dimethylformamide (20 ml ) and benzyl bromide (1.2 ml) added. The orange solution was stirred at ambient temperature for 3 hours. The dimethylformamide was evaporated in vacuo, the residue diluted with ethyl acetate (50 ml), which solution was washed with water (50 ml) dried over MgSO$_4$ and evaporated. The residue was diluted with a little ethanol, when the benzyl 9-phthalimidodeoxyclavulanate (starting material) crystallized: recovery 0.7 g. After removal of this material, the solution was evaporated and subjected to gradient elution chromatography or silica gel using ethyl acetate and cyclohexane graded from 1:1 to 2:1 ratio. Fractions containing the product [benzyl 9-(2'-benzyloxycarbonyl - benzamide) deoxyclavulanate] were combined and evaporated to yield 0.6g of of the required product.

It had i.r. (film ) 3370, 1805, 1730 (broad) 1660 cm $^{-1}$.
Nmr (CDCl$_3$) δ 2.98 (1H,d,J 17 Hz, 6-β-C$\underline{H}$), 3.41 (1H, dd, J 17 and 3 Hz, 6-α-C$\underline{H}$), 3.89 (2H,d,J 7Hz, 9-C$\underline{H}_2$), 4.62 (1H ,t,J, 7Hz, [8—C$\underline{H}$), 4.96 (1H,S,3—C$\underline{H}$) 5.12 (2H,S,C$\underline{H}_2$C$_6$H$_5$) 5.23 (2H,S,C$\underline{H}_2$C$_6$H$_5$), 5.60 (1H,d,J 3 Hz,5-C$\underline{H}$) 5.70 (1H, bs, N$\underline{H}$), 7.0–8.0 (14H, m, aromatic $\underline{H}$)

EXAMPLE 19

Benzyl 9-(N-benzyloxycarbonyl)chloroacetamidodeoxyclavulanate

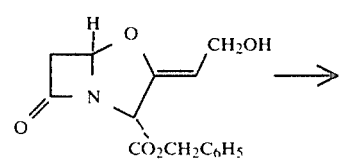

-continued

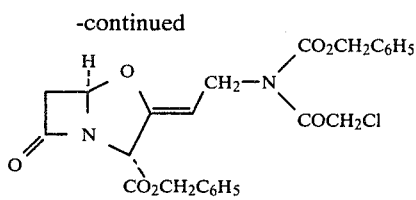

To a stirred solution of benzylclavulanate(1.45 g)triphenylphoshine(1.8 g) and benzyl N-chloroacetyl carbomate (2.27 g) in tetrahydrofuran (25 ml) at 5° C., was added diethyl azodicarboxylate (1.2 ml). After 30 minutes, the solvent was removed by evaporation under reduced pressure, and the residue triturated with 3:2 cyclohexane-ethylacetate (25ml). The insoluble materials were filtered off, and the filtrate re-evaporated. The residue was subjected to chromatography on silica gel using 3:1 cyclohexene-ethyl acetate as eluent. Fractions containing the product were combined and re-chromatographed using gradient elution: 3:1 graded to 1:1 ratio of cyclohexane-ethyl acetate. Fractions containing the pure material were combined and evaporated, to yield 180 mg of the desired product. I.r. (film) 1803 ($\beta$-lactam C=O) 1740 cm$^{-1}$ (broad, imide C=O, and C=C); nmr(CDCl$_3$) 2.73(1H,d,J 17 Hz,6-$\beta$-C$\underline{H}$), 3.27(1H,dd, J 17 and 3 Hz,6-$\alpha$-C$\underline{H}$), 4.41 (2H,d,J 7Hz,9-C$\underline{H}_2$), 4.51 (2H,s,C$\underline{H}_2$Cl) 4.93 (1H,s3-C$\underline{H}$), and 7.23 (10H,s,2XC$_6$$\underline{H}_5$). (Benzyl N-chloroacetylcarbomate was prepared by the reaction of the commercially available chloroacetylisocyanate with a dichoromethane solution of benzyl alcohol).

EXAMPLE 20

Lithium 9-N-phenoxycarbonylaminodeoxyclavulanate

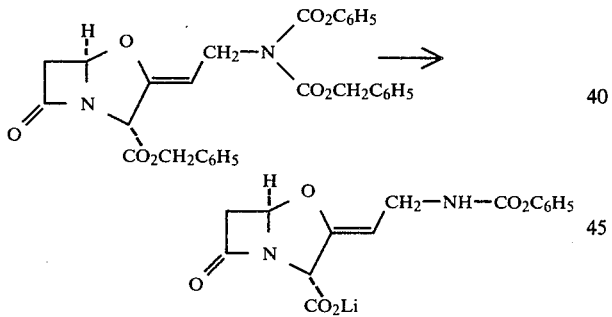

A solution of the benzyl 9-(N-phenoxycarbonyl)benzyloxycarbonylaminodeoxyclavulanate (320 mg) in redistilled tetrahydrofuran (10 ml) containing water (0.1 ml) was hydrogenated at ambient temperature and pressure over 10% palladised charcoal (120 mg) during 30 minutes. (After 20 minutes a sample showed no starting material by tlc.). The catalyst was removed by filtration through celite, the bed washed with tetrahydrofuran (10 ml) and with water (10 ml). The filtrate was diluted with water (20 ml) neutralised to pH 8.0 with 1M aqueous LiOH solution, and evaporated to near dryness under reduced pressure. The syrupy residue was triturated with acetone (20 ml) cooled at 2°–3° for 30 mins., filtered off solid, washed with acetone and with ether and dried in vacuo, to yield 125 mg of colourless microcrystalline solid. Ir. (Nujol mull) 3330 (broad) 1785, 1712, 1618 cm$^{-1}$.

EXAMPLE 21

Benzyl 9-N-succinimidodeoxyclavulanate

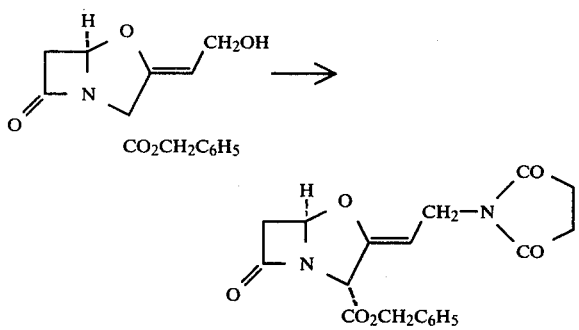

To a stirred solution of benzyl clavulanate (0.963 g), succinimide (0.33 g), triethyl phosphite (0.4 ml) in tetrahydrofuran (20 ml) at 5° C. was added diethyl azodicarboxylate (0.7 g). A zone on tlc slowly appeared at the same Rf as an authentic sample of the title ester (see Example 3).

EXAMPLE 22

9-N-Benzamidodeoxyclavulanic acid, Lithium 9-N-Benzamidodeoxyclavulanic acid and Benzyl 9-N-benzamidodeoxyclavulanic acid

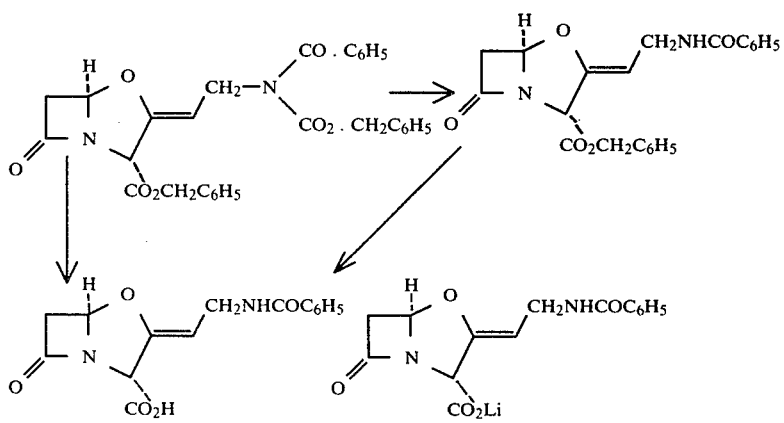

A solution of benzyl N-benzyloxycarbonyl-9-N-benzamidodeoxyclavulanate (800 mg) in tetrahydrofuran (40 ml), ethanol (4 ml) and water (0.1 ml) was hydrogenated over pre-reduced 10% palladised barium sulphate (400 mg) for a total of 40 minutes at ambient temperature and pressure. T.l.c. then showed starting material, origin material and an intermediate zone. The catalyst was removed by filtration, the filtrate diluted with an equal volume of water and titrated to pH 7.0 with aqueous LiOH solution. The solution was evaporated to dryness in vacuo, and the residue triturated with acetone-ether. The lithium 7-benzamidodeoxyclavulanate was filtered off, and dried, to yield a crystalline solid (275 mg). (I.r. identical to previously prepared material described in Example 6.) The organic filtrate was evaporated to dryness and subjected to elution chromatography on silica gel using 1:1 ethyl acetate-cyclohexane as eluents. The less polar material was found to be unreacted starting material (179 mg). The fractions containing the more polar compound were combined and evaporated, when the residue solidified to colourless crystalline solid benzyl 9-N-benzamidodeoxyclavulanate (56 mg) (identical to the compound prepared by benzylation of the lithium salt described in Example 25).

EXAMPLE 23

4-Chlorophenoxymethyl 9-N-succinimidodeoxyclavulanate

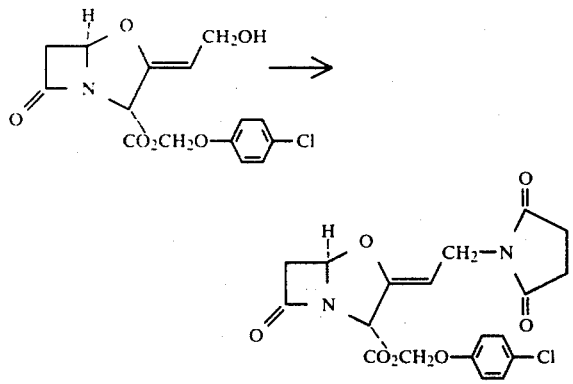

To a solution of 4-chlorophenoxymethyl clavulanate (0.5 g), triphenylphosphine (0.46 g), and succinimide (0.14 g) in tetrahydrofuran (10 ml), cooled and stirred at about 0° C., was added diethyl azodicarboxylate (0.31 ml). The mixture was stirred for 15 mins., then evaporated in vacuo. Ethyl acetate-cyclohexane (30 ml, 2:3), was added and the mixture cooled, the insolubles filtered off and the filtrate reevaporated. The residue was subjected to gradient elution chromatography on silica gel using ethyl acetate and cyclohexane graded from 1:3 to 1:1 as elution solvent. Fractions containing the product, by tlc, were combined and evaporated to an oil, which was rechromatographed, eluting with 1:1 ethyl acetate-cyclohexane. Fractions containing the pure product were combined and evaporated to an oil (70 mg). Ir (film) 1715, 1770, and 1805 cm$^{-1}$; δ (CDCl$_3$) 2.62 (4H, s, CH$_2$—CH$_2$), 3.09 (1H, d, J 17Hz, 6-β-CH) 3.48 (1H, dd, J 17 and 3Hz, 6-α-CH), 4.10 (2H, d, J 7Hz, 9-CH$_2$) 4.68 (1H, t, J 7Hz, 8—CH) 5.02 (1H, s, 3—CH) 5.70, 5.82 (2H, ABq J 6HZ,OCH$_2$), 5.69 (1H, bs, 5-CH), 6.92-7.29 (4H, ABq, J 9Hz, C$_6$H$_4$).

EXAMPLE 24

Lithium 9-N-succinimidodeoxyclavulanate

4-Chlorophenoxymethyl 9-N-succinimidodeoxyclavulanate (30 mg) in water (5 ml) and tetrahydrofuran (5 ml) was hydrolysed at pH 9 with 0.1 M aqueous LiOH solution. About 0.6 ml was taken up. The solution was evaporated in vacuo and the residue triturated with acetone (20 ml). The acetone was decanted, and the insoluble lithium salt washed by decantation with a further 5 ml of acetone and then 5 ml of ether. The remainder was dried in vacuo, to give the required product in somewhat crude form (as shown by comparison of its n.m.r. spectrum with that of an authentic sample prepared as described in Example 4).

EXAMPLE 25

Benzyl 9-N-benzamidodeoxyclavulanate

Lithium 9-N-benzamidodeoxyclavulanate (860 mg) was dissolved in the minimum amount of dry dimethylformamide, and benzyl bromide (0.48 g) was added. After 90 mins tlc showed zones due inter alia to the desired ester. The solution was evaporated in vacuo and the residue partitioned between ethyl acetate and water. The ethyl acetate extract was dried over anhydrous sodium sulphate, filtered, and evaporated to an oil which largely solidified. It was dissolved in ethyl acetate and subjected to column chromatography on silica gel using 1:1 ethyl acetate and cyclohexane as eluent. A partial purification was effected. Fractions containing the title compound were combined, evaporated and rechromatographed using 2:1 cyclohexane and ethyl acetate as eluent. Fractions containing only the title compound (by tlc) were combined and evaporated to dryness in vacuo to yield the title compound as a colourless crystalline solid (0.137 g).

Ir (Nujol mull)=1641, 1701, 1743, 1799, 3299 cm$^{-1}$.
N.M.R. δ 3.07 (1H, d, J 17Jz, 6βCH), 3.57 (1H, dd, J 17 3H$_3$, 6αCH).
CDCl$_3$ 4.15(2H, t, J 7Hz, 9-CH$_2$), 4.84 (1H, t, J 7H$_3$, 8CH), 5.10 (1H, s, 3CH), 5.25 (2H, s, CH$_2$—Ph), 5.72 (1H, d, J 3H$_3$, 5CH), 6.12 (1H, broad s, NH), 7.27 to 7.80 (1OH, m, C$_6$H$_5$×2).

EXAMPLE 26

Benzyl 9-N-maleimidodeoxyclavulanate

To a solution of benzyl clavulanate (2.89 g), triphenylphosphine (3.14 g) and maleimide (0.97 g) in benzene (40 ml) and tetrahydrofuran (50 ml), stirred at 5° C., was added diethyl azodicarboxylate (2.1 ml). A new zone somewhat less polar than benzyl clavulanate appeared on t.l.c. Insoluble materials were filtered off and the filtrate evaporated to dryness. Ethanol (~50 ml) was added and the mixture refrigerated at 2°-3° C. for about 1 hour. A colourless crystalline solid was filtered off and dried in vacuo to yield benzyl 9-N-maleimidodeoxyclavulanate (1.22 g) m.p. 120° C. I.r. ν (nujol mull) 1790, 1740 and 1695 cm$^{-1}$; δ (CDCl$_3$) 3.06 (1H, d, J 17Hz, 6-β-CH), 3.43 (1H, dd, J 17 and 3Hz, 6-α-CH), 4.13 (2H, d, J 7Hz, 9-CH$_2$), 4.67 (1H, t, J 7Hz, 8-CH), 4.98 (1H, s, 3-CH), 5.12 (2H, s, CH$_2$C$_6$H$_5$), 5.65 (1H, d, J 3Hz, 5-CH), 6.60 (2H, s, CH=CH) and 7.26 (5H, s, C$_6$H$_5$).

EXAMPLE 27

9-N-Benzyloxycarbonyldeoxyclavulanic acid Lithium 9-N-benzyldeoxycarbonylaminodeoxyclavulanate

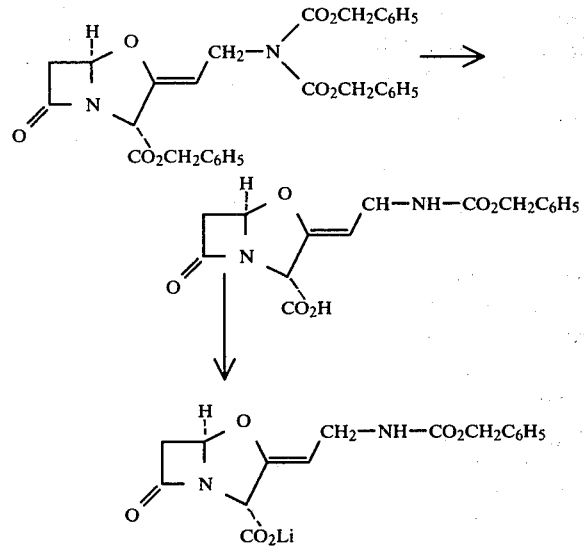

A solution of benzyl 9-N,N-dibenzyloxycarbonylaminodeoxyclavulanate (1.0 g) in tetrahydrofuran (100 ml) containing water (0.1 ml) was hydrogenated over 10% palladised charcoal (0.33 g) (Engelhard 4505) for 3 minutes. Afer this time, uptake of hydrogen, which had initially been very fast, became much slower. The reaction was stopped, diluted with ethyl acetate (100 ml), and the catalyst removed by filtration through celite; the filter bed was washed with ethyl acetate (100 ml). The filtrate and washings contained the 9-N-benzyloxycarbonylaminodeoxyclavulanate. These were combined and washed with 0.4% aqueous $NaH_2PO_4.2H_2O$ (150 ml). The organic layer was mixed with water (100 ml) and titrated to pH 7.0 with 1 M aqueous lithium hydroxide solution. The aqueous layer was separated and evaporated to dryness in vacuo. It was triturated with acetone (5 ml), and the precipitated solid filtered off, washed with acetone and air-dried, to yield lithium 9-N-benzyloxycarbonylaminodeoxyclavulanate as a colourless crystalline solid (0.223 g).

I.r. (nujol mull) $\nu_{max}$ 1541, 1623, 1696, 1796 and 3320 cm$^{-1}$; δ (D$_2$O) 2.95 (1H, d, J 17Hz, 6-β-CH), 3.49 (1H, dd, J 17 and 3Hz, 6-α-C$\underline{H}$), 3.76 (2H, d, J 7Hz, 9-C$\underline{H}_2$), 4.5–4.75 (HOD partly obscures 8-CH), 4.85 (1H, s, 3-C$\underline{H}$), 5.08 (2H, s, PhC$\underline{H}_2$), 5.62 (1H, d, J 3Hz, 5-C$\underline{H}$) and 7.35 (5H, s, C$_6$$\underline{H}_5$).

EXAMPLE 28

Methyl 9-N-benzyloxycarbonylaminodeoxyclavulanate

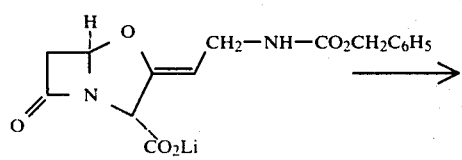

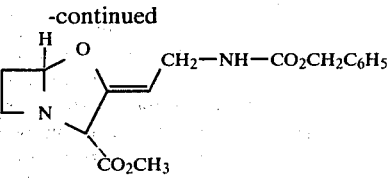

A suspension of lithium 9-N-benzyloxycarbonylaminodeoxyclavulanate (100 mg) in dimethylformamide (12 ml) was treated with iodomethane (two portions of 0.02 ml) and water (0.1 ml). After twenty minutes, tlc showed the presence of a less polar component. The solvent was evaporated in vacuo, and ethyl acetate and water (20 ml of each) added. The ethyl acetate layer was separated, dried over Na$_2$SO$_4$ and evaporated (some 50 mg of starting material was recovered from the aqueous phase by evaporation). The residue was chromatographed on silica gel using ethyl acetate and cyclohexane (1:1) as eluents. Fractions containing the product (by tlc) were combined and evaporated to a colourless oil, which later crystallised (45 mg).

I.r. (film) $\nu_{max}$ 3365, 1800, 1695–1758 (broad) cm$^{-1}$.
n.m.r. (CDCl$_3$): δ 3.00 (1H, d, J 17Hz, 6-β-C$\underline{H}$), 3.46 (1H, dd, J 17 and 3Hz, 6-α-C$\underline{H}$), 3.52 (3H, s, C$\underline{H}_3$), 3.86 (2H, t, J 7Hz, 9-C$\underline{H}_2$), 4.74 (1H, t, J 7Hz, 8-C$\underline{H}$), 4.98 (1H, s, 3-C$\underline{H}$), 5.08 (2H, s, PhC$\underline{H}_2$), 5.66 (1H, d, J 3Hz, 5-C$\underline{H}$) and 7.30 (5H, s, C$_6$$\underline{H}_5$).

EXAMPLE 29

Lithium 9-benzyloxycarbonylaminodeoxyclavulanate and benzyl 9-benzyloxycarbonylaminodeoxyclavulanate

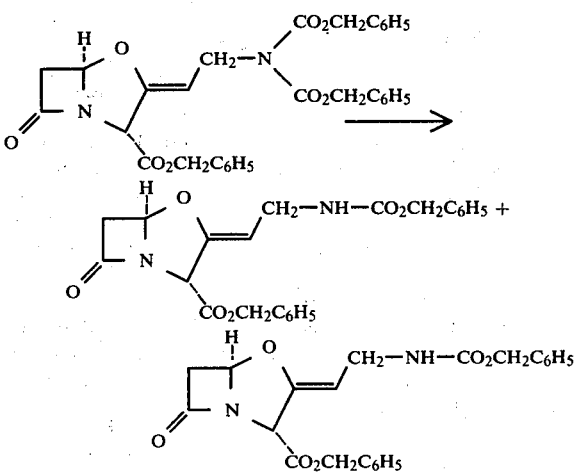

Benzyl 9-N,N-bisbenzyloxycarbonylaminodeoxyclavulanate (1.0 g) in redistilled tetrahydrofuran (110 ml) containing water (ca 0.1 ml) was hydrogenated over 10% palladised barium sulphate (1.0 g, prehydrogenated) for 10 minutes at ambient temperature and pressure (80 cm$^3$ of hydrogen was absorbed); at this time, tlc (1:1 ethyl acetate-cyclohexane) showed the presence of a trace of starting material, a less polar zone and origin material. The catalyst was removed by filtration through celite, the filtrate diluted with water (an equal volume) and titrated to pH 7 with 1 M aqueous lithium hydroxide. The whole was evaporated to dryness in vacuo, and the residue triturated with acetone.

The insoluble material was filtered off, washed with acetone and dried in vacuo, to yield lithium benzyloxycarbonylaminodeoxyclavulanate (120 mg). The filtrate was evaporated and the starting material separated from the required product by column chromatography on silica gel using 1:1 ethyl acetatecyclohexane as eluent. The product eluted after a trace of starting material, and fractions containing it (by tlc) were combined and evaporated to dryness, to yield benzyl benzyloxycarbonylaminodeoxyclavulanate (23 mg) as a colourless crystalline solid.

I.R. (Nujol mull) 3310, 1800, 1740 and 1690 cm$^{-1}$.

EXAMPLE 30

Lithium 9-(4-methyl-3,5-dioxo-1,2,4-oxadiazolidin-2-yl)deoxyclavulanate

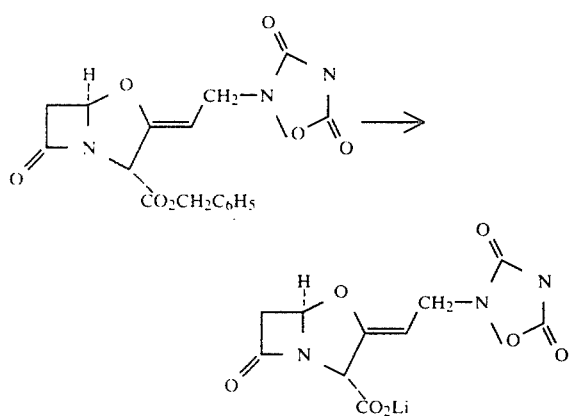

A solution of benzyl 9-(4-methyl-3,5-dioxo-1,2,4-oxadiazolidin-2-yl)deoxyclavulanate (100 mg) in tetrahydrofuran (10 ml) containing water (<0.1 ml) was hydrogenated over 10% palladised charcoal (0.03 g) for 20 min. at ambient temperature and pressure. The catalyst was removed by filtration through celite; the bed was washed with water (20 ml) and the combined filtrates neutralised to pH 7 with 0.1 M aqueous lithium hydroxide. The solution was evaporated to dryness in vacuo, acetone (15 ml) added, and the precipitated solid filtered off, washed with ether (5 ml) and dried in vacuo, to yield lithium 9-(4-methyl-3,5-dioxo-1,2,4-oxadiazolidin-2-yl)deoxyclavulanate (40 mg).

I.r. (nujol) 1820, 1793, 1725 and 1615 cm$^{-1}$, and δ (D$_2$O) 3.12 (3H, s, N-C$\underline{H}_3$), 3.13 (1H, d, J 17Hz, 6-β-C$\underline{H}$), 3.61 (1H, dd, J 17 and 3Hz, 6-α-C$\underline{H}$), 4.47 (2H, d, J 7Hz, 9-C$\underline{H}_2$), 6.88 (1H, t, J 7Hz, 8-C$\underline{H}$), 4.99 (1H, s, 3-C$\underline{H}$), and 5.78 (1H, d, J 3Hz, 5-C$\underline{H}$).

EXAMPLE 31

Sodium 9-benzyloxycarbonylaminodeoxyclavulanate

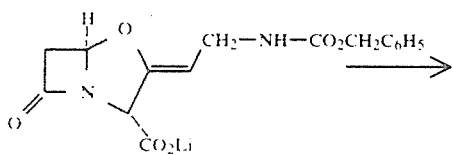

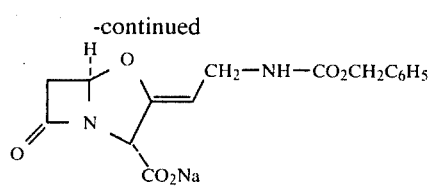

A solution of lithium 9-benzyloxycarbonylaminodeoxyclavulanate (30 mg) in water (5 ml) was passed slowly through a column of 'Amberlite' IR 120 standard grade, Na$^+$form (10 ml of wet resin). A total of 50 ml of eluate was collected. It was evaporated to circa 1 ml under reduced pressure, diluted with n-propanol (2 ml) and then further evaporated almost to dryness. It was treated with acetone (4 ml), triturated, cooled to 2°–3° C. for 1 hr, filtered off, washed with acetone and with ether, to yield sodium 9-benzyloxycarbonylaminodeoxyclavulanate (20 mg) as a pale buff crystalline solid. I.r. (nujol mull) 3380 (broad) 1785, 1695 and 1625 cm$^{-1}$.

EXAMPLE 32

Lithium 9-chloroacetamidodeoxyclavulanate

A solution of benzyl 9-N-benzyloxycarbonyl-chloroacetamidodeoxyclavulanate (150 mg) in tetrahydrofuran (20 ml) containing water (4 ml) and 5% aqueous lithium hydrogen carbonate (0.8 ml) was hydrogenated over 10% palladised charcoal (50 ml) at ambient temperature and pressure for 20 mins. At this time tlc showed the absence of starting material. The catalyst was removed by filtration, the filtrate evaporated to dryness, and triturated with acetone. The product was filtered off, washed with acetone and ether and dried in vacuo, to yield the title compound (80 mg) as a colourless solid.

It had Ir (Nujol mull) 3300-3400 (broad), 1782, 1640-1665 (broad) and 1620 cm$^{-1}$; δ (D$_2$O) 3.02 (1h, d, J 17Hz, 6-β-C$\underline{H}$), 3.46 (1H, dd, J 17 and 3Hz, 6-α-C$\underline{H}$), 3.83 (2H, d, J 7Hz, 9-C$\underline{H}$), 4.01 (2H, s, C$\underline{H}_2$Cl), 4.93 (1H, t, J 7Hz, 8-C$\underline{H}$), 4.94 (1H, s, 3-C$\underline{H}$), and 5.64 (1H, d, J 3Hz, 5-C$\underline{H}$).

EXAMPLE 33

Compositions a. 9-Aminodeoxyclavulanic acid (pure crystalline form) may be granulated with 1% magnesium stearate. This granulate may then be mixed with an equal weight of microcrystalline cellulose (Avicell) and the resulting mixture granulated. These granules may then be used in a conventional rotary tabletting machine to produce a batch of 5000 tablets containing on average:

| | |
|---|---|
| 9-Aminodeoxyclavulanic acid | 250 mg |
| Microcrystalline cellulose | 252.5 mg |
| Magnesium stearate | 2.5 mg | b. 9-Aminodeoxyclavulanic acid (pure crystalline form) may be granulated with 1% magnesium stearate and 2% sodium starch glycollate (Primojel). These granules may be filled into capsules on a conventional machine to produce a batch of 5000 capsules containing on average:

| | |
|---|---|
| 9-Aminodeoxyclavulanic acid | 250 mg |
| Sodium starch glycollate | 5 mg |

| -continued | |
|---|---|
| Magnesium stearate | 2.5 mg | c. 9-Aminodeoxyclavulanic acid (pure crystalline form) may be granulated with 1% magnesium stearate. Amoxycillin may be granulated with 1% magnesium stearate. The two granulates may be mixed together with 4% microcrystalline cellulose (Avicell) and regranulated. These granules may be tabletted on a conventional rotary tabletting machine to produce a batch of 5000 tablets containing on average:

| 9-Aminodeoxyclavulanic acid | 125 mg |
|---|---|
| Amoxycillin trihydrate (equivalent to amoxycillin) | 300 mg |
| Magnesium stearate | 4.25 mg |
| Microcrystalline cellulose | 17 mg |

EXAMPLE 34

Compositions a. Sterile sodium 9-benzyloxycarbonylaminodeoxyclavulanate (200 mg) may be filled into a glass vial in a steril manner. The vial may then be capped.

b. Sterile sodium benzamidodeoxyclavulanate (125 mg) may be filled into a glass vial in a sterile manner. The vial may then be capped.

The above compositions may be dissolved with shaking in 2 ml sterile water to prepare injectable compositions.

The following results were obtained against an inter peritoneal infection in mice due to *Escherichia coli* JT39. Dosing was by subcutaneous injection of a solution (pH 7.2 phosphase buffer) 1 and 5 hours post infection:

| Medicament | $CD_{50}$ |
|---|---|
| Amoxycillin alone | >1000 mg/kg × 2 |
| Amoxycillin + 5 mg/kg benzamidodeoxyclavulanate | 12.2 mg/kg × 2 |

What we claim is:

1. A compound of the formula (II):

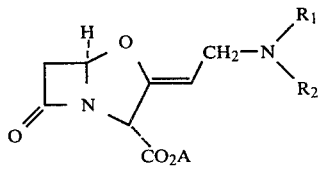

wherein A is a group such that $CO_2A$ is carboxylic acid, a pharmaceutically acceptable salt thereof or an ester thereof and A is a group of the formula $A_1$ or $CHA_2A_3$ wherein $A_1$ is alkyl of 1 to 6 carbon atoms unsubstituted or substituted by alkoxy or acyloxy of 1 to 7 carbon atoms; $A_2$ is alkenyl of up to 5 carbon atoms or phenyl unsubstituted or substituted by fluorine, chlorine, bromine, nitro or alkyl or alkoxyl of up to 4 carbon atoms; and $A_3$ is hydrogen, alkyl of up to 4 carbon atoms or phenyl unsubstituted or substituted by fluorine, chlorine, bromine, nitro or alkyl or alkoxyl of up to 4 carbon atoms; $R_1$ is $COR_4$ or $OR_5$ wherein $R_4$ is lower alkyl, lower alkenyl, lower alkyl aryl or aryl and $R_5$ is $CO_2R_6$, $COR_6$ or $SO_2R_6$ wherein $R_6$ is lower alkyl, lower alkenyl, lower alkyl aryl or aryl; and $R_2$ is $COR_8$ wherein $R_8$ is lower alkyl, lower alkenyl, lower alkyl aryl or aryl; when $R_1$ is $COR_4$ and $R_2$ is $COR_8$, $R_4$ and $R_8$ are joined so that the $N(COR_4)$ $COR_8$ moiety is a 5-, 6-, or 7-membered heterocyclic ring or said ring to which is fused a phenyl ring unsubstituted or substituted by one or two lower alkyl, lower alkoxyl, fluorine or chlorine, wherein $R_4$ and $R_8$ are as above defined; when $R_1$ is $OR_5$ and $R_2$ is $COR_8$, $R_5$ and $R_8$ are joined so that the $N(OR_5)$ $COR_8$ moiety is a 5-, 6-, or 7-membered heterocyclic ring, wherein $R_5$ and $R_8$ are as above defined.

2. A compound of the formula (III):

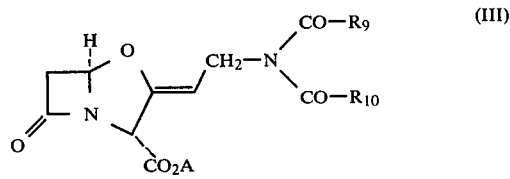

wherein A is a group such that $CO_2A$ is carboxylic acid or a pharmaceutically acceptable salt thereof; $R_9$ is joined to $R_{10}$ so that the N $(CO.R_9)$ $COR_{10}$ moiety is a 5-, 6-, or 7-membered heterocyclic ring or such ring to which is fused a phenyl ring substituted or unsubstituted by one or two substituents selected from the group consisting of lower alkoxyl, lower alkyl, fluorine and chlorine, $R_9$ and $R_{10}$ being selected from the group consisting of lower alkyl, lower alkenyl, lower alkyl aryl and aryl.

3. A compound of the formula (IV):

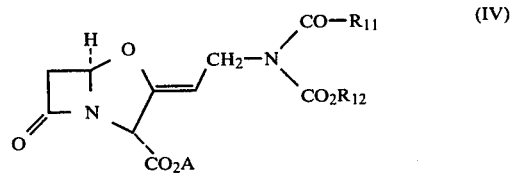

wherein A is a group such that $CO_2A$ is carboxylic acid or a pharmaceutically acceptable salt thereof; $R_{11}$ is joined to $R_{12}$ so that the $N(CO.R_{11})$ $CO_2R_{12}$ moiety is a 5-, 6- or 7-membered heterocyclic ring or such ring to which is fused a phenyl ring unsubstituted or substituted by one or two substituents selected from the group consisting of lower alkoxyl, lower alkyl, fluorine and chlorine, $R_{11}$ and $R_{12}$ being selected from the group consisting of lower alkyl, lower alkenyl, lower alkyl aryl and aryl.

4. A compound according to claim 2 wherein $CO_2A$ is carboxylic acid.

5. A compound according to claim 2 wherein $CO_2A$ is a pharmaceutically acceptable salt of carboxylic acid.

6. A compound according to claim 5 wherein the salt is the sodium, potassium, calcium, magnesium or ammonium salt.

7. A compound of the formula (III):

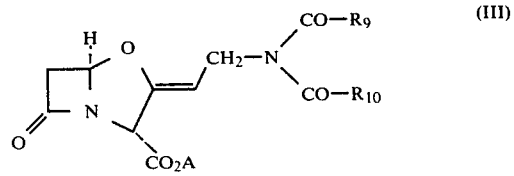

wherein A is lithium, and $R_9$ is joined to $R_{10}$ so that the $N(CO.R_9)COR_{10}$ moiety is a 5-, 6-, or 7-membered heterocyclic ring or such ring to which is fused a phenyl ring unsubstituted or substituted by one or two substituents selected from the group consisting of lower alkoxyl, lower alkyl, fluorine and chlorine, $R_9$ and $R_{10}$ being selected from the group consisting of lower alkyl, lower alkenyl, lower alkyl aryl and aryl.

8. A compound according to claim 2 wherein $CO_2A$ is a non-toxic ester.

9. A compound according to claim 8 wherein A is a group of the formula $A_1$ or $CHA_2A_3$ wherein $A_1$ is alkyl of 1 to 6 carbon atoms unsubstituted or substituted by alkoxy or acyloxy of 1 to 7 carbon atoms; $A_2$ is alkenyl of up to 5 carbon atoms or phenyl unsubstituted or substituted by fluorine, chlorine, bromine, nitro or alkyl or alkoxyl of up to 4 carbon atoms; and $A_3$ is hydrogen, alkyl of up to 4 carbon atoms or phenyl unsubstituted or substituted by fluorine, chlorine, bromine, nitro or alkyl or alkoxyl of up to 4 carbon atoms.

10. A compound according to claim 9 wherein $A_1$ is methyl, methoxymethyl, acetoxymethyl, acetoxymethyl, acetoxyethyl, phthalidyl, ethoxycarbonyloxymethyl or α-ethoxycarbonyloxyethyl.

11. A compound according to claim 9 wherein $A_2$ is phenyl.

12. A compound according to claim 9 wherein $A_2$ is 4-methoxyphenyl.

13. A compound according to claim 9 wherein $A_2$ is 4-nitrophenyl.

14. A compound according to claim 9 wherein $A_3$ is hydrogen.

15. A compound according to claim 8 wherein the ester is the benzyl ester.

16. A compound according to claim 8 wherein the ester is the 4-methoxybenzyl ester.

17. A compound according to claim 3 wherein $CO_2A$ is carboxylic acid or a non-toxic salt thereof.

18. A compound according to claim 3 wherein $CO_2A$ is carboxylic acid.

19. A compound according to claim 3 wherein $CO_2A$ is a pharmaceutically acceptable salt of carboxylic acid.

20. A compound according to claim 19 wherein the salt is the sodium, potassium, calcium, magnesium or ammonium salt.

21. A compound according to claim 19 wherein the salt is the lithium salt.

22. A compound according to claim 3 wherein $CO_2A$ is a non-toxic ester.

23. A compound according to claim 22 wherein A is a group of the formula $A_1$ or $CHA_2A_3$ wherein $A_1$ is alkyl of 1 to 6 carbon atoms unsubstituted or substituted by alkoxy or acyloxy of 1 to 7 carbon atoms; $A_2$ is alkenyl of up to 5 carbon atoms or phenyl unsubstituted or substituted by fluorine, chlorine, bromine, nitro or alkyl or alkoxyl of up to 4 carbon atoms; and $A_3$ is hydrogen, alkyl of up to 4 carbon atoms or phenyl unsubstituted or substituted by fluorine, chlorine, bromine, nitro or alkyl or alkoxyl of up to 4 carbon atoms.

24. A compound according to claim 23 wherein $A_1$ is methyl, methoxymethyl, acetoxymethyl, acetoxymethyl, acetoxyethyl, phthalidyl, ethoxycarbonyloxymethyl or α-ethoxycarbonyloxyethyl.

25. A compound according to claim 23 wherein $A_2$ is phenyl.

26. A compound according to claim 23 wherein $A_2$ is 4-methoxyphenyl.

27. A compound according to claim 23 wherein $A_2$ is 4-nitrophenyl.

28. A compound according to claim 23 wherein $A_3$ is hydrogen.

29. A compound according to claim 22 wherein the ester is the benzyl ester.

30. A compound according to claim 28 wherein the ester is the 4-methoxybenzyl ester.

31. A compound according to claim 1 wherein $R_1$ is $OR_5$ wherein $R_5$ is $CO_2R_6$, $COR_6$ or $SO_2R_6$ wherein $R_6$ is lower alkyl, lower alkenyl, lower alkyl aryl or aryl.

32. A compound according to claim 2 wherein $R_9$ and $R_{10}$ are linked to form $-CH_2.CH_2-$, $-CH=CH-$, $-CH_2.CH_2.CH_2-$, phenylene, methoxyphenylene, methylphenylene, $-NH-CO-$, or $-N(CH_3)-CO-$.

33. A compound according to claim 5 wherein $R_{11}$ and $R_{12}$ are linked to form $-CH_2.CH_2-$, $-CH=CH-$, $-CH_2.CH_2.CH_2-$, phenylene or methoxyphenylene.

34. A compound according to claim 1 wherein $CO_2A$ is carboxylic acid or a pharmaceutically acceptable salt thereof.

35. A compound according to claim 1 wherein $CO_2A$ is carboxylic acid.

36. A compound according to claim 3 wherein $CO_2A$ is a pharmaceutically acceptable salt of carboxylic acid.

37. A compound according to claim 36 wherein the salt is the sodium, potassium, calcium, magnesium or ammonium salt.

38. A compound according to claim 1 wherein A is a group of the formula $A_1$ or $CHA_2A_3$ wherein $A_1$ is alkyl of 1–6 carbon atoms unsubstituted or substituted by alkoxyl or acyloxyl of 1–7 carbon atoms; $A_2$ is alkenyl of up to 5 carbon atoms or phenyl unsubstituted or substituted by fluorine, chlorine, bromine, nitro or alkyl or alkoxyl of up to 4 carbon atoms; and $A_3$ is hydrogen, of up to 4 carbon atoms or phenyl unsubstituted or substituted by fluorine, chlorine, bromine, nitro or alkyl or alkoxyl of up to 4 carbon atoms.

39. A compound according to claim 38 wherein $A_1$ is methyl, methoxymethyl, acetoxymethyl, acetoxyethyl, phthalidyl, ethoxycarbonyloxymethyl or α-ethoxycarbonyloxyethyl.

40. A compound according to claim 38 wherein $A_2$ is phenyl.

41. A compound according to claim 38 wherein $A_2$ is 4-methoxyphenyl.

42. A compound according to claim 38 wherein $A_2$ is 4-nitrophenyl.

43. A compound according to claim 38 wherein $A_3$ is hydrogen.

44. A compound according to claim 1 wherein the ester is the benzyl ester.

45. A compound according to claim 1 wherein the ester is the 4-methoxybenzyl ester.

46. The compound according to claim 1 which is benzyl 9-N-phthalimidodeoxyclavulanate.

47. The compound according to claim 1 which is sodium 9-N-phthalimidodeoxyclavulanate.

48. The compound according to claim 1 which is potassium 9-N-phthalimidodeoxyclavulanate.

49. The compound according to claim 1 which is calcium 9-N-phthalimidodeoxyclavulanate.

50. The compound according to claim 1 which is benzyl 9-N-succinimidodeoxyclavulanate.

51. The compound according to claim 1 which is benzyl 9-(1-methyl-2,4,5-trioxoimidazolid-3-yl) deoxyclavulanate.

52. The compound according to claim 1 which is benzyl 9-(4-methyl-3,5-dioxo-1,2,4-oxadiazolidin-2-yl)-deoxyclavulanate.

53. The compound according to claim 1 which is di-sodium 9-phthalamidodeoxyclavulanic acid.

54. The compound according to claim 1 which is 4-chlorophenoxymethyl 9-N-succinimidodeoxyclavulanate.

55. The compound 1 lithium 9-N-phthalimidodeoxyclavulanate.

56. The compound 1 lithium 9-N-succinimidodeoxyclavulanate.

57. A compound of the formula (II):

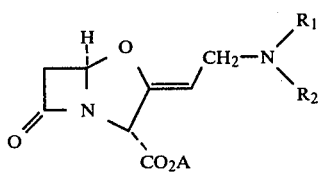 (II)

wherein A is lithium, $R_1$ is $COR_4$ or $OR_5$ wherein $R_4$ is lower alkyl, lower alkenyl, lower alkyl aryl or aryl and $R_5$ is $CO_2R_6$, $COR_6$ or $SO_2R_6$ wherein $R_6$ is lower alkyl, lower alkenyl, lower alkyl aryl or aryl; and $R_2$ is $COR_8$ wherein $R_8$ is lower alkyl, lower alkenyl, lower alkyl aryl or aryl; when $R_1$ is $COR_4$ and $R_2$ is $COR_8$, $R_4$ and $R_8$ are joined so that the $N(COR_4) COR_8$ moiety is a 5-, 6-, or 7-membered heterocyclic ring or said ring to which is fused a phenyl ring unsubstituted or substituted by one or two lower alkyl, lower alkoxyl, fluorine or chlorine, wherein $R_4$ and $R_8$ are as above defined; when $R_1$ is $OR_5$ and $R_2$ is $COR_8$, $R_5$ and $R_8$ are joined so that the $N(OR_5)COR_8$ moiety is a 5-,6-, or 7-membered heterocyclic ring, wherein $R_5$ and $R_8$ are as above defined.

58. A compound of the formula (IV):

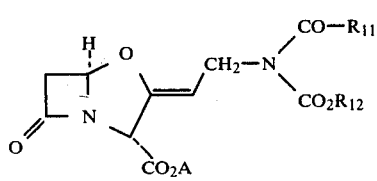 (IV)

wherein A is lithium, $R_{11}$ is joined to $R_{12}$ so that the $N(CO.R_{11}) CO_2R_{12}$ moiety is a 5-, 6- or 7-membered heterocyclic ring or such ring to which is fused a phenyl ring unsubstituted or substituted by one or two substituents selected from the group consisting of lower alkoxyl, lower alkyl, fluorine and chlorine. $R_{11}$ and $R_{12}$ being selected from the group consisting of lower alkyl, lower alkenyl, lower alkyl aryl and aryl.

59. A pharmaceutical composition useful for treating bacterial infections in humans and animals which comprises an antibacterially effective amount of a compound of the formula (II):

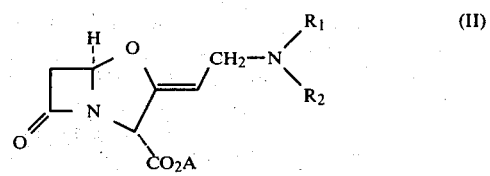 (II)

wherein A is a group such that $CO_2A$ is carboxylic acid, a pharmaceutically acceptable salt thereof or ester thereof and A is a group of the formula $A_1$ or $CHA_2A_3$ wherein $A_1$ is alkyl of 1 to 6 carbon atoms unsubstituted or substituted by alkoxy or acyloxy of 1 to 7 carbon atoms; $A_2$ is alkenyl of up to 5 carbon atoms or phenyl unsubstituted or substituted by fluorine, chlorine, bromine, nitro or alkyl or alkoxyl of up to 4 carbon atoms; and $A_3$ *is hydrogen, alkyl of up to* 4 carbon atoms or phenyl unsubstituted or substituted by fluorine, chlorine, bromine, nitro or alkyl or alkoxyl of up to 4 carbon atoms; $R_1$ is $COR_4$ or $OR_5$ wherein $R_4$ is lower alkyl, lower alkenyl, lower alkyl aryl or aryl and $R_5$ is $CO_2R_6$, $COR_6$ or $SO_2R_6$ wherein $R_6$ is lower alkyl, lower alkenyl, lower alkyl aryl or aryl; and $R_2$ is $COR_8$ wherein $R_8$ is lower alkyl, lower alkenyl, lower alkyl aryl or aryl; when $R_1$ is $COR_4$ and $R_2$ is $COR_8$, $R_4$ and $R_8$ are joined so that the $N(COR_4) COR_8$ moiety is a 5-, 6-, or 7-membered heterocyclic ring or said ring to which is fused a phenyl ring unsubstituted or substituted by one or two lower alkyl, lower alkoxyl, fluorine or chlorine, wherein $R_4$ and $R_8$ are as above defined; when $R_1$ is $OR_5$ and $R_2$ is $COR_8$, $R_5$ and $R_8$ are joined so that the $N(OR_5) COR_8$ moiety is a 5-, 6-, or 7- membered heterocyclic ring, wherein $R_5$ and $R_8$ are as above defined; in combination with a pharmaceutically acceptable carrier.

60. A composition according to claim 59 wherein the compound is of the formula (III):

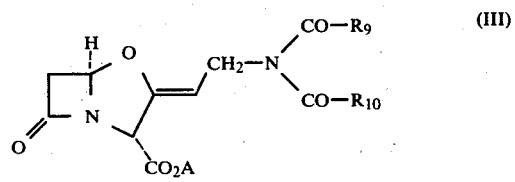 (III)

wherein A is a group such that $CO_2A$ is carboxylic acid or a pharmaceutically acceptable salt thereof; $R_9$ is joined to $R_{10}$ so that the $N(CO.R_9) COR_{10}$ moiety is a 5-, 6-, or 7-membered heterocyclic ring or such ring to which is fused a phenyl ring unsubstituted or substituted by one or two substituents selected from the group consisting of lower alkoxyl, lower alkyl, fluorine and chlorine, $R_9$ and $R_{10}$ being selected from the group consisting of lower alkyl, lower alkenyl, lower alkyl aryl or aryl.

61. A composition according to claim 59 wherein the compound is of the formula (IV):

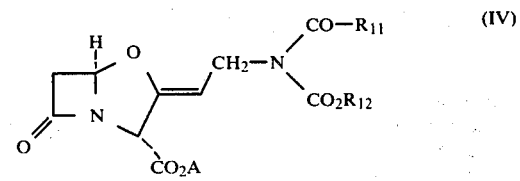 (IV)

wherein A is a group such that $CO_2A$ is carboxylic acid or a pharmaceutically acceptable salt thereof; $R_{11}$ is joined to $R_{12}$ so that the $N(CO.R_{11}) CO_2R_{12}$ moiety is a 5-, 6-, or 7-membered heterocyclic ring or such ring to which is fused a phenyl ring unsubstituted or substituted by one or two substituents selected from the group consisting of lower alkoxyl, lower alkyl, fluorine and chlorine, $R_{11}$ and $R_{12}$ being selected from the group consisting of lower alkyl, lower alkenyl, lower alkyl aryl and aryl.

62. A composition according to claim 60 wherein $CO_2A$ is carboxylic acid or a non-toxic salt thereof.

63. A composition according to claim 60 wherein $CO_2A$ is carboxylic acid.

64. A composition according to claim 60 wherein $CO_2A$ is a pharmaceutically acceptable salt of carboxylic acid.

65. A composition according to claim 64 wherein the salt is the sodium, potassium, calcium, magnesium or ammonium salt.

66. A composition according to claim 61 wherein $CO_2A$ is carboxylic acid.

67. A composition according to claim 61 wherein $CO_2A$ is a pharmaceutically acceptable salt of carboxylic acid.

68. A composition according to claim 67 wherein the salt is the sodium, potassium, calcium, magnesium or ammonium salt.

69. A composition according to claim 59 in oral administration form.

70. A composition according to claim 59 in parentral administration form.

71. A composition according to claim 59 in topical application form.

72. A composition according to claim 60 wherein $R_9$ and $R_{10}$ are linked and form $-CH_2.CH_2-$, $-CH=CH-$, $-CH_2.CH_2.CH_2-$, phenylene, methoxyphenylene, methylphenylene, $-NH-CO-$, or $-N(CH_3)-CO-$.

73. A composition according to claim 61 wherein $R_{11}$ and $R_{12}$ are linked to form $-CH_2.CH_2-$, $-CH=CH-$, $-CH_2.CH_2.CH_2-$, phenylene or methoxyphenylene.

74. A composition according to claim 59 wherein $CO_2A$ is carboxylic acid or a pharmaclutically acceptable salt thereof.

75. A composition according to claim 59 wherein $CO_2A$ is carboxylic acid.

76. A composition according to claim 59 wherein $CO_2A$ is a pharmaceutically acceptable salt of carboxylic acid.

77. A composition according to claim 76 wherein the salt is the sodium, potassium, calcium, magnesium or ammonium salt.

78. A composition according to claim 59 wherein $A_1$ is methyl, methoxymethyl, acetoxymethyl, acetoxyethyl, phthalidyl, ethoxycarbonyloxymethyl or α-ethoxycarbonyloxyethyl.

79. A composition according to claim 59 wherein $A_2$ is phenyl.

80. A composition according to claim 59 wherein $A_2$ is 4-methoxyphenyl.

81. A composition according to claim 59 wherein $A_2$ is 4-nitrophenyl.

82. A composition according to claim 59 wherein $A_3$ is hydrogen.

83. A composition according to claim 59 wherein the ester is the benzyl ester.

84. A composition according to claim 59 wherein the ester is the 4-methyloxybenzyl ester.

85. A composition according to claim 59 wherein the compound is benzyl 9-N-phthalimidodeoxyclavulanate.

86. A composition according to claim 59 wherein the compound is sodium 9-N-phthalimidodeoxyclavulanate.

87. A composition according to claim 59 wherein the compound is potassium 9-N-phthalimidodeoxyclavulanate.

88. A composition according to claim 59 wherein the compound is calcium 9-N-phthalimidodeoxyclavulanate.

89. A composition according to claim 59 wherein the compound is benzyl 9-N-succinimidodeoxyclavulanate.

90. A composition according to claim 59 wherein the compound is benzyl 9-(1-methyl-2,4,5-trioxoimidazolid-3-yl) deoxyclavulanate.

91. A composition according to claim 59 wherein the compound is benzyl 9-(4-methyl-3,5-dioxo-1,2,4-oxadiazolidin-2-yl)-deoxyclavulanate.

92. A composition according to claim 59 wherein the compound is di-sodium 9-phthalamidodeoxyclavulanic acid.

93. A composition according to claim 59 wherein the compound is 4-chlorophenoxymethyl 9-N-succinimidodeoxyclavulanate.

94. A composition according to claim 59 wherein the compound is lithium 9-(4-methyl-3,5-dioxo-1,2,4-oxadiazolidin-2yl)deoxyclavulanate.

95. A method of treating bacterial infections in humans and animals which comprises administering to a human or animal in need thereof an antibacterially effective amount of a compound of the formula (II):

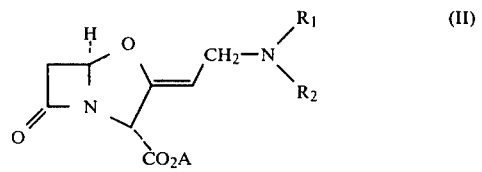

wherein A is a group such that $CO_2A$ is carboxylic acid, a non-toxic salt thereof or non-toxic ester thereof; $R_1$ is $COR_4$ or $OR_5$ wherein $R_4$ is lower alkyl, lower alkenyl, lower alkyl aryl or aryl and $R_5$ is $CO_2R_6$, $COR_6$ or $SO_2R_6$ wherein $R_6$ is lower alkyl, lower alkenyl, lower alkyl aryl or aryl; and $R_2$ is $COR_8$ wherein $R_8$ is lower alkyl, lower alkenyl, lower alky aryl or aryl; when $R_1$ is $COR_4$ and $R_2$ is $COR_8$, $R_4$ and $R_8$ are joined so that the $N(COR_4) COR_8$ moiety is a 5-, 6-, or 7-membered heterocyclic ring or said ring to which is fused a phenyl ring unsubstituted or substituted by one or two lower alkyl, lower alkoxyl, fluorine or chlorine; or when $R_1$ is $OR_5$ and $R_2$ is $COR_8$, $R_5$ and $R_8$ are joined so that the $N(OR_5) COR_8$ moiety is a 5-, 6-, or 7-membered heterocyclic ring.

96. A method according to claim 95 wherein $R_1$ is $OR_5$ wherein $R_5$ is $CO_2R_6$, $COR_6$ or $SO_2R_6$ wherein $R_6$ is lower alkyl, lower alkenyl, lower alkyl aryl or aryl.

97. A method according to claim 95 wherein the compound is of the formula (III):

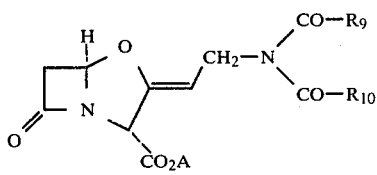

wherein A is a group such that $CO_2A$ is carboxylic acid or a pharmaceutically acceptable salt thereof; $R_9$ is joined to $R_{10}$ so that the $N(CO.R_9)$ $COR_{10}$ moiety is a 5-, 6-, or 7-membered heterocylic ring or such ring to which is fused a phenyl ring unsubstituted or substituted by one or two substituents selected from the group consisting of lower alkoxyl, lower alkyl, fluorine and chlorine, $R_9$ and $R_{10}$ being selected from the group consisting of lower alkyl, lower alkenyl, lower alkyl aryl or aryl.

98. A method according to claim 97 wherein $R_9$ and $R_{10}$ are linked and form —$CH_2.CH_2$—, —CH=CH—, —$CH_2.CH_2.CH_2$—, phenylene, methoxyphenylene, methylphenylene, methylphenylene, —NH—CO—, or —N($CH_3$)—CO—.

99. A method according to claim 95 wherein the compound is of the formula (IV):

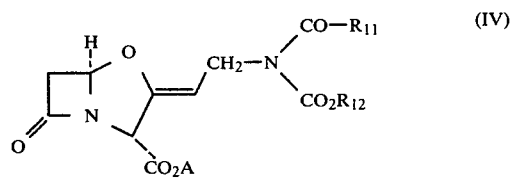

wherein A is a group such that $CO_2A$ is carboxylic acid or a pharmaceutically acceptable salt thereof; $R_{11}$ is joined to $R_{12}$ so that the $N(CO.R_{11})$ $CO_2R_{12}$ moiety is a 5-, 6-, or 7-membered heterocyclic ring or such ring to which is fused a phenyl ring unsubstituted or substituted by one or two substituents selected from the group consisting of lower alkoxy, lower alkyl, fluorine and chlorine, $R_{11}$ and $R_{12}$ being selected from the group consisting of lower alkyl, lower alkenyl, lower alkyl aryl and aryl.

100. A method according to claim 99 wherein $R_{11}$ and $R_{12}$ are linked to form —$CH_2.CH_2$—, —CH=CH—, —$CH_2.CH_2.CH_2$—, phenylene or methoxyphenylene.

101. A method according to claim 95 wherein $CO_2A$ is carboxylic acid or a pharmaceutically acceptable salt thereof.

102. A method according to claim 95 wherein $CO_2A$ is carboxylic acid.

103. A method according to claim 95 wherein $CO_2A$ is a pharmaceutically acceptable salt of carboxylic acid.

104. A method according to claim 103 wherein the salt is the sodium, potassium, calcium, magnesium or ammonium salt.

105. A method according to claim 95 wherein $A_1$ is methyl, methoxymethyl, acetoxymethyl, acetoxyethyl, phthalidyl, ethoxycarbonyloxymethyl or α-ethoxycarbonyloxyethyl.

106. A method according to claim 95 wherein $A_2$ is phenyl.

107. A method according to claim 95 wherein $A_2$ is 4-methoxyphenyl.

108. A method according to claim 95 wherein $A_2$ is 4-nitrophenyl.

109. A method according to claim 95 wherein $A_3$ is hydrogen.

110. A method according to claim 95 wherein the ester is the benzyl ester.

111. A method according to claim 95 wherein the ester is the 4-methoxybenzyl ester.

112. A method according to claim 95 wherein the compound is benzyl 9-N-phthalimidodeoxyclavulanate.

113. A method according to claim 95 wherein the compound is sodium 9-N-phthalimidodeoxyclavulanate.

114. A method according to claim 95 wherein the compound is potassium 9-N-phthalimidodeoxyclavulanate.

115. A method according to claim 95 wherein the compound is calcium 9-N-phthalimidodeoxyclavulanate.

116. A method according to claim 95 wherein the compound is benzyl 9-N-succinimidodeoxyclavulanate.

117. A method according to claim 95 wherein the compound is benzyl 9-(1-methyl-2,4,5-trioxoimidazolid-3-yl) deoxyclavulanate.

118. A method according to claim 95 wherein the compound is benzyl 9-(4-methyl-3,5-dioxo-1,2,4-oxadiazolidin-2-yl) deoxyclavulanate.

119. A method according to claim 95 wherein the compound is di-sodium 9-phthalamidodeoxyclavulanic acid.

120. A method according to claim 95 wherein the compound is 4-chlorophenoxymethyl 9-N-succinimidodeoxyclavulanate.

121. A method according to claim 95 wherein the compound is benzyl 9-N-benzamidodeoxyclavulanate.

122. A method according to claim 95 wherein the compound is benzyl 9-N-maleimidodeoxyclavulanate.

123. A method according to claim 95 wherein the compound is 9-N-benzyloxycarbonyldeoxyclavulanic acid.

124. A method according to claim 95 wherein the compound is lithium 9-N-benzyl-deoxycarbonylaminodeoxyclavulanate.

125. A method according to claim 95 wherein the compound is methyl 9-N-benzyloxycarbonylaminodeoxyclavulanate.

126. A method according to claim 95 wherein the compound is lithium 9-benzyloxycarbonylaminodeoxyclavulanate.

127. A method according to claim 95 wherein the compound is benzyl 9-benzyloxycarbonylaminodeoxyclavulanate.

128. A method according to claim 95 wherein the compound is sodium 9-benzyloxycarbonylaminodeoxyclavulanate.

129. A method according to claim 95 wherein the compound is lithium 9-chloroacetamidodeoxyclavulanate.

130. A method according to claim 95 wherein the administration is oral.

131. A method according to claim 95 wherein the administration is parenteral.

132. A method according to claim 95 wherein the administration is by topical application.

133. A method according to claim 97 wherein $CO_2A$ is carboxylic acid.

134. A method according to claim 97 wherein $CO_2A$ is a pharmaceutically acceptable salt of carboxylic acid.

135. A method according to claim 134 wherein the salt is the sodium, potassium, calcium, magnesium or ammonium salt.

136. A method according to claim 99 wherein $CO_2A$ is carboxylic acid or a pharmaceutically acceptable salt thereof.

137. A method according to claim 99 wherein $CO_2A$ is carboxylic acid.

138. A method according to claim 99 wherein $CO_2A$ is a pharmaceutically acceptable salt of carboxylic acid.

139. A method according to claim 138 wherein the salt is the sodium, potassium, calcium, magnesium or ammonium salt.

140. A method according to claim 138 wherein the salt is the lithium salt.

141. A method according to claim 99 wherein $CO_2A$ is a non-toxic ester.

142. A method according to claim 141 wherein A is a group of the formula $A_1$ or $CHA_2A_3$ wherein $A_1$ is alkyl or 1 to 6 carbon atoms unsubstituted or substituted by alkoxy or acyloxy of 1 to 7 carbon atoms; $A_2$ is alkenyl of up to 5 carbon atoms or phenyl unsubstituted or substituted by fluorine, chlorine, bromine, nitro or alkyl or alkoxyl of up to 4 carbon atoms; and $A_3$ is hdyrogen, alkyl of up to 4 carbon atoms or phenyl unsubstituted or substituted by fluorine, chlorine, bromine, nitro or alkyl or alkoxyl of up to 4 carbon atoms.

143. A method according to claim 142 wherein $A_1$ is methyl, methoxymethyl, acetoxymethyl, acetoxymethyl, acetoxyethyl phthalidyl, ethoxycarbonyloxymethyl or α-ethoxycarbonyloxyethyl.

144. A method according to claim 142 wherein $A_2$ is phenyl.

145. A method according to claim 142 wherein $A_2$ is 4-methoxyphenyl.

146. A method according to claim 142 wherein $A_2$ is 4-nitrophenyl.

147. A method according to claim 141 wherein $A_3$ is hydrogen.

148. A method according to claim 141 wherein the ester is the benzyl ester.

149. A method according to claim 141 wherein the ester is the 4-methoxybenzyl ester.

* * * * *